United States Patent
Bennett et al.

(10) Patent No.: US 7,335,676 B2
(45) Date of Patent: *Feb. 26, 2008

(54) METHODS FOR TREATING INFLAMMATORY CONDITIONS OR INHIBITING JNK

(75) Inventors: Brydon L. Bennett, San Diego, CA (US); Shripad S. Bhagwat, San Diego, CA (US); Anthony M. Manning, San Diego, CA (US); Brion W. Murray, San Diego, CA (US); Eoin C. O'Leary, San Diego, CA (US); Yoshitaka Satoh, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/738,640

(22) Filed: Dec. 16, 2003

(65) Prior Publication Data

US 2004/0176434 A1    Sep. 9, 2004

Related U.S. Application Data

(63) Continuation of application No. 10/395,810, filed on Mar. 24, 2003, which is a continuation-in-part of application No. 09/642,557, filed on Aug. 18, 2000.

(60) Provisional application No. 60/240,928, filed on Aug. 19, 1999.

(51) Int. Cl.
 A61K 31/415    (2006.01)
(52) U.S. Cl. .................................................. 514/406
(58) Field of Classification Search ............... 514/222.5
 See application file for complete search history.

(56) References Cited

U.S. PATENT DOCUMENTS

| | | | |
|---|---|---|---|
| 4,198,518 A | 4/1980 | Tzikas | |
| 4,202,827 A | 5/1980 | Tzikas | |
| 4,556,654 A | 12/1985 | Showalter et al. | |
| 6,162,613 A | 12/2000 | Su et al. | |

FOREIGN PATENT DOCUMENTS

| | | |
|---|---|---|
| CS | 146895 | 2/1972 |
| DE | 1257149 | 12/1967 |
| EP | 0 208 211 | 1/1987 |
| GB | 1293557 | 9/1970 |
| GB | 1404969 | 8/1973 |
| GB | 1576217 | 7/1977 |
| WO | WO 99/53927 | 10/1999 |
| WO | WO 00/35909 | 6/2000 |
| WO | WO 01/12609 | 2/2001 |
| WO | WO 01/12621 A1 | 2/2001 |
| WO | WO 02/085396 | 10/2002 |
| WO | PCT/US04/009209 | 8/2004 |

OTHER PUBLICATIONS

Akamatsu, CA 58:27252, 1963.
Ames et al., 1987, "An integrated concept of amebicidal action: electron transfer and oxy radicals", Free Radical Biol. Med. 3:85-96.
Aspenström et al., 1996, "Two GTPases, Cdc42 and Rac, bind directly to a protein implicated in the immunodeficiency disorder Wiskott-Aldrich syndrome", Curr. Biol. 6:70-75.
Bogoyevitch et al., 2004, Targeting the JNK MAPK cascade for inhibition: basic science and therapeutic potential: Biochimica Et Biophysica Acta, vol. 1697(1-2) pp. 89-101.
Chen et al., 1996, "Activation and inhibition of the AP-1 complex in human breast cancer cells", Mol. Carcinogenesis 15:215-226.
Dong et al., 1998, "Defective T cell differentiation in the absence of Jnk1", Science 282:2092-2095.
Faris et al., 1996, "Regulation of interleukin-2 transcription by inducible stabile expression of dominant negative and dominant active mitogen-activated protein kinase kinase in Jurkat T cells", J. Biol. Chem. 271:27366-27373.
Galushko and Dokunikhin, 1977, "Pyrazoloanthrone derivatives I. Reactivity of 3-aminopyrazoloanthrone", Khimiya Geterotsiklicheskikh Soedinenii, 7:956-961.
Gum et al., 1997, "Regulation of 92 kDa type IV collagenase expression by the jun aminoterminal kinase- and the extracellular signal-regulated kinase- dependent signaling cascades", Oncogene 14:1481-1493.
Gvon et al., 1994, "Amino-imino tautomerism and intramolecular cyclization of 4,9-diamino-1, 10-anthraquinone-1-tosylimines" Dokl. Akad. Nauk, 334:465-468 (in Russian with English abstract).
Han et al., 1999, "Jun N-terminal kinase in rheumatoid arthritis", J. Pharmacol. Exp. Therap. 291:124-130.
Hartley et al., 1988, "Characteristics of the interaction of anthrapyrazole anticancer agents with deoxyribonucleic acids: structural requirements for DNA binding, intercalation, and photosensitization", Mol. Pharmacol. 33:265-271.
Hibi et al., 1993, "Identification of an oncoprotein- and UV-responsive protein kinase that binds and potentiates the c-Jun activation domain", Genes Dev. 7:2135-2148.

(Continued)

*Primary Examiner*—Brian Kwon
(74) *Attorney, Agent, or Firm*—Jones Day

(57) ABSTRACT

This invention generally relates to methods for treating or preventing an inflammatory disease or disorder comprising administering to a patient in need thereof an effective amount of a Pyrazoloanthrone Derivative having the following structure:

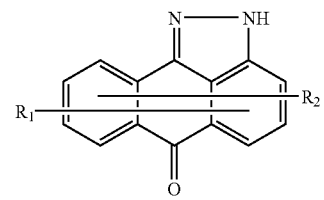

or a pharmaceutically acceptable salt thereof, wherein $R_1$ and $R_2$ are as defined herein.

6 Claims, 7 Drawing Sheets

OTHER PUBLICATIONS

Hirosumi et al., 2002, "A central role for JNK in obesity and insulin resistance", Letters to Nature 420:333-336.

Ishizuka et al., 1997, "Mast cell tumor necrosis factor α production is regulated by MEK kinases", Proc. Natl. Acad. Sci. USA 94:6358-6363.

Ivanova et al., 1997, "XPS investigation of electronic structure of pyrazolanthrone and its derivatives" Poverkhnost, 4-5:193-201.

Judson, 1992, "The anthrapyrazoles: a new class of compounds with clinical activity in breast cancer", Semin. Oncol. 19:687-694.

Karin et al., 1997, "AP-1 function and regulation", Curr. Opin. Cell. Biol. U9:240-246.

Lange-Carter et al., 1993, "A divergence in the MAP kinase regulatory network defined by MEK kinase and Raf", Science 260:315-319.

Laakso et al., CA 51-76969, 1957.

Li et al., 1996, "Blocked signal transduction to the ERK and JNK protein kinases in anergic CD4+ T cells", Science 271:1272-1276.

Li et al., 1996, "The Ras-JNK pathway is involved in shear-induced gene expression", Mol. Cell. Biol. 16:5947-5954.

Lin et al., 1995, "Identification of a dual specificity kinase that activates the Jun kinases and p38-Mpk2", Science 268:286-290.

Manning and Mercurio, 1997, "Transcription inhibitors in inflammation", Exp. Opin. Invest. Drugs 6:555-567.

Milne et al., 1995, "p53 is phosphorylated in vitro and in vivo by an ultraviolet radiation-induced protein kinase characteristic of the c-Jun kinase, JNK1", J. Biol. Chem. 270:5511-5518.

Mohit et al., 1995, "p493F12 kinase: a novel MAP kinase expressed in a subset of neurons in the human nervous system", Neuron 14:67-78.

Mosby et al. CA 54:80551, 1960.

Nishina et al., 1997, "Impaired CD28-mediated interleukin 2 production and proliferation in stress kinase SAPK/ERK1 kinase (SEK1)/mitogen-activated protein kinase kinase 4 (MKK4)-deficient T lymphocytes", J. Exp. Med. 186:941-953.

Okamoto et al., 1997, "Selective activation of the JNK/AP-1 pathway in Fas-mediated apoptosis of rheumatoid arthritis synoviocytes", Arthritis & Rheumatism 40:919-926.

Pombo et al., 1994, "The stress-activated protein kinases are major c-Jun amino-terminal kinases activated by ischemia and reperfusion", J. Biol. Chem. 269:26546-26551.

Raitano et al., 1995, "The Bcr-Abl leukemia oncogene activates Jun kinase and requires Jun for transformation", Proc.Natl. Acad. Sci. USA 92:11746-11750.

STN International® CAPLUS Database, Accession No. 1989: Showalter et al. (1988).

STN International® CAPLUS Database, Accession No. 1997:491798; Ivanova et al., Poverkhnost (1997), (4-5), 193-201.

STN International® CAPLUS Database, Accession No. 1994:30709, Sokolyuk et al., Zh, Org. Khim. (1992), 28(10), 2193-200.

STN International® CAPLUS Database, Accession No. 1973:406796, Arient, Patent No. CS 146895 (1973).

Sabapathy et al., 1999, "JNK2 is required for efficient T-cell activation and apoptosis but not for normal lymphocyte development", Curr. Biol. 9:116-125.

Showalter et al., 1987, "Anthrapyrazole anticancer agents. Synthesis and structure-activity relationships against murine leukemias", J. Med. Chem. 30:121-131.

Showalter et al., 1984, "5-[(Aminoalkyl)amino]-substituted anthral[1,9-cd]pyrazol-6(2H)-ones as novel anticancer agents. Synthesis and biological evaluation", J. Med. Chem. 27:253-255.

Showalter et al, 1988, "Design, Tumor Biology, and Biochemical Pharmacology of Anthrapyrazoles" Bioact. Mol. Chapter VI:201-243.

Singh and Shah, 1978, "Reactions of 2,2'-ethylene-bis-anthrapyrazolone", Indian J. -Chem. 16B:100-102.

Sokolyuk et al., 1992, "Synthesis and photochemical properties of peri-phenoxy derivatives of 6H-anthra[1,9-cd]-6-pyrazolone (pyrazolanthrone)", Zhurnal Organicheskoi Khimii 28:2193-200.

Spiegelman et al., 1993, "Regulation of Adipocyte Gene Expression in Differentiation and Syndromes of Obesity/Diabetes", J. of Biol. Chem. 268:6823-6826.

Su et al., 1994, "JNK is involved in signal integration during costimulation of T lymphocytes", Cell 77:727-736.

Swantek et al., 1997, "Jun N-terminal kinase/stress-activated protein kinase (JNK/SAPK) is required for lipopolysaccharide stimulation of tumor necrosis factor alpha (TNF-α) translation: glucocorticoids inhibit TNF-α translation by blocking JNK/SAPK", Mol. Cell. Biol. 17:6274-6282.

Szabo et al., 1996, "Altered cJUN expression: an early event in human lung carcinogenesis", Cancer Res. 56:305-315.

Tournier et al., 1997, "Mitogen-activated protein kinase kinase 7 is an activator of the c-Jun NH2-terminal kinase", Proc. Natl. Acad. Sci. USA 94:7337-7342.

Whitmarsh and Davis, 1996, "Transcription factor AP-1 regulation by mitogen-activated protein kinase signal transduction pathways", Mol. Med. 74:589-607.

Yan et al., 1994, "Activation of stress-activated protein kinase by MEKK1 phosphorylation of its activator SEK1", Nature 372:798-800.

Yang et al., 1998, "Differentiation of CD4+ T cells to Th1 cells requires MAP kinase JNK2", Immunity 9:575-585.

Yin et al., 1997, "Tissue-specific pattern of stress kinase activation in ischemic/reperfused heart and kidney", J. Biol. Chem. 272:19943-19950.

CAS No. 130:153598d for Gwon et al., 1998 "Direct amination of 6H-anthra(9,1-cd)isothiazol-6-one 2,2-dioxides", Dokl. Akad. Nauk, 359:357-61.

CAS No. 86:121031v for Shah et al., 1976 "Thiocyanation of 1-aminoanthraquinones", Indian J. Chem. 14B:625-626.

CAS No. 102:205411f for Mitsubishi Chemical Industries Co., Ltd., JP 60 028,454.

CAS No. 104:208328m for Mitsubishi Chemical Industries Co., Ltd., JP 60 250,052.

CAS No. 103:143360y for Mitsubishi Chemical Industries Co., Ltd., JP 60 092,355.

Web page printout of Dec. 18, 2002 for http://www.calbiochem.com/Products/ProductDetail_CBCB.asp?catNO=420119 (cat. No. 420119).

CAS No. 1989:185177, Showalter et al. (1988).

Bennett, et al., "SP600125, an anthrapyrazolone inhibitor of Jun N-terminal kinase," *PNAS* 24(98):13681-13686 (2001).

METHODS FOR TREATING INFLAMMATORY CONDITIONS OR INHIBITING JNK

This application is a continuation of U.S. application Ser. No. 10/395,810 filed Mar. 24, 2003, which is a continuation-in-part of U.S. application Ser. No. 09/642,557, filed Aug. 18, 2000, which claims the benefit of U.S. Provisional Application No. 60/240,928, filed Aug. 19, 1999, each of which is incorporated by reference herein in its entirety.

FIELD OF THE INVENTION

This invention is generally directed to Pyrazoloanthrones and derivatives thereof which have utility over a wide range of indications, including activity as Jun N-terminal kinase inhibitors, and related compositions and methods.

BACKGROUND OF THE INVENTION

The Jun N-terminal kinase (JNK) pathway is activated by exposure of cells to environmental stress or by treatment of cells with pro-inflammatory cytokines. Targets of the JNK pathway include the transcription factors c-jun and ATF2 (Whitmarsh A. J., and Davis R. J. *J. Mol. Med.* 74:589-607, 1996). These transcription factors are members of the basic leucine zipper (bZIP) group that bind as homo- and hetero-dimeric complexes to AP-1 and AP-1-like sites in the promoters of many genes (Karin M., Liu Z. G. and Zandi E. *Curr Opin Cell Biol* 9:240-246, 1997). JNK binds to the N-terminal region of c-jun and ATF-2 and phosphorylates two sites within the activation domain of each transcription factor (Hibi M., Lin A., Smeal T., Minden A., Karin M. *Genes Dev.* 7:2135-2148, 1993; Mohit A. A., Martin M. H., and Miller C. A. *Neuron* 14:67-78, 1995]. Three JNK enzymes have been identified as products of distinct genes (Hibi et al, supra; Mohit et al., supra). Ten different isoforms of JNK have been identified. These represent alternatively spliced forms of three different genes: JNK1, JNK2 and JNK3. JNK1 and 2 are ubiquitously expressed in human tissues, whereas JNK3 is selectively expressed in the brain, heart and testis (Dong, C., Yang, D., Wysk, M., Whitmarsh, A., Davis, R., Flavell, R. *Science* 270:1-4, 1998). Gene transcripts are alternatively spliced to produce four-JNK1 isoforms, four JNK2 isoforms and two-JNK3 isoforms. JNK1 and 2 are expressed widely in mammalian tissues, whereas JNK3 is expressed almost exclusively in the brain. Selectivity of JNK signaling is achieved via specific interactions of JNK pathway components and by use of scaffold proteins that selectively bind multiple components of the signaling cascade. JIP-1 (JNK-interacting protein-1) selectively binds the MAPK module, MLK→JNKK1→JNK.12, 13 It has no binding affinity for a variety of other MAPK cascade enzymes. Different scaffold proteins are likely to exist for other MAPK signaling cascades to preserve substrate specificity.

JNKs are activated by dual phosphorylation on Thr-183 and Tyr-185. JNKK1 (also known as MKK4) and JNKK2 (MKK7), two MAPKK level enzymes, can mediate JNK activation in cells (Lin A., Minden A., Martinetto H., Claret F.-Z., Lange-Carter C., Mercurio F., Johnson G. L., and Karin M. *Science* 268:286-289, 1995; Tournier C., Whitmarsh A. J., Cavanagh J., Barrett T., and Davis R. J. *Proc. Nat. Acad. Sci. USA* 94:7337-7342, 1997). JNKK2 specifically phosphorylates JNK, whereas JNKK1 can also phosphorylate and activate p38. Both JNKK1 and JNKK2 are widely expressed in mammalian tissues. JNKK1 and JNKK2 are activated by the MAPKKK enzymes, MEKK1 and 2 (Lange-Carter C. A., Pleiman C. M., Gardner A. M., Blumer K. J., and Johnson G. L. *Science* 260:315-319, 1993; Yan M., Dai J. C., Deak J. C., Kyriakis J. M., Zon L. I., Woodgett J. R., and Templeton D. J. *Nature* 372:798-781, 1994). Both MEKK1 and MEKK2 are widely expressed in mammalian tissues.

Activation of the JNK pathway has been documented in a number of disease settings, providing the rationale for targeting this pathway for drug discovery. In addition, molecular genetic approaches have validated the pathogenic role of this pathway in several diseases. For example, autoimmune and inflammatory diseases arise from the over activation of the immune system. Activated immune cells express many genes encoding inflammatory molecules, including cytokines, growth factors, cell surface receptors, cell adhesion molecules and degradative enzymes. Many of these genes are regulated by the JNK pathway, through activation of the transcription factors AP-1 and ATF-2, including TNF-$\alpha$, IL-2, E-selectin and matrix metalloproteinases such as collagenase-1 (Manning A. M. and Mercurio F. *Exp Opin Invest Drugs* 6: 555-567, 1997; International Publication No. WO 99/53927, published Oct. 28, 1999). Monocytes, tissue macrophages and tissue mast cells are key sources of TNF-$\alpha$ production. The JNK pathway regulates TNF-$\alpha$ production in bacterial lipopolysaccharide-stimulated macrophages, and in mast cells stimulated through the FceRII receptor (Swantek J. L., Cobb M. H., Geppert T. D. *Mol. Cell. Biol.* 17:6274-6282, 1997; Ishizuka, T., Tereda N., Gerwins, P., Hamelmann E., Oshiba A., Fanger G. R., Johnson G. L., and Gelfland E. W. *Proc. Nat. Acad. Sci. USA* 94:6358-6363, 1997). Inhibition of JNK activation effectively modulates TNF-$\alpha$ secretion from these cells. The JNK pathway therefore regulates production of this key proinflammatory cytokine. Matrix metalloproteinases (MMPs) promote cartilage and bone erosion in rheumatoid arthritis, and generalized tissue destruction in other autoimmune diseases. Inducible expression of MMPs, including MMP-3 and MMP-9, type II and IV collagenases, are regulated via activation of the JNK pathway and AP-1 (Gum, R., Wang, H., Lengyel, E., Juarez, J., and Boyd, D. *Oncogene* 14:1481-1493, 1997). In human rheumatoid synoviocytes activated with TNF-$\alpha$, IL-1, or Fas ligand the JNK pathway is activated (Han Z., Boyle D. L., Aupperle K. R., Bennett B., Manning A. M., Firestein G. S. *J. Pharm. Exp. Therap.* 291:1-7, 1999; Okamoto K., Fujisawa K., Hasunuma T., Kobata T., Sumida T., and Nishioka K. *Arth & Rheum* 40: 919-92615, 1997). Inhibition of JNK activation results in decreased AP1 activation and collagenase-1 expression (Han et al., supra). The JNK pathway therefore regulates MMP expression in cells involved in rheumatoid arthritis.

Inappropriate activation of T lymphocytes initiates and perpetuates many autoimmune diseases, including asthma, inflammatory bowel disease and multiple sclerosis. The JNK pathway is activated in T cells by antigen stimulation and CD28 receptor co-stimulation and regulates production of the growth factor IL-2 and cellular proliferation (Su B., Jacinto E., Hibi M., Kallunki T., Karin M., Ben-Neriah Y. *Cell* 77:727-736, 1994; Faris M., Kokot N., Lee L., and Nel A. E. *J. Biol. Chem.* 271:27366-27373, 1996). Peripheral T cells from mice genetically deficient in JNKK1 show decreased proliferation and IL-2 production after CD28 co-stimulation and PMA/Ca2+ ionophore activation, providing important validation for the role of the JNK pathway in these cells (Nishina H., Bachmann M., Oliveria-dos-Santos A. J., et al. *J. Exp. Med.* 186: 941-953, 1997). It is known that T cells activated by antigen receptor stimulation in the absence of accessory cell-derived co-stimulatory signals lose the capacity to synthesize IL-2, a state called clonal anergy. This is an important process by which autoreactive T cell populations are eliminated from the peripheral circulation. Of note, anergic T cells fail to activate the JNK pathway in response to CD3- and CD28-receptor co-stimulation, even though expression of the JNK enzymes is unchanged (Li W., Whaley C. D., Mondino A., and Mueller D. L. *Science* 271: 1272-1276, 1996). Recently, the examination of JNK deficient mice revealed that the JNK pathway plays a key role in T cell activation and differentiation to T helper 1 and 2 cell types. JNK1 or JNK2 knockout mice develop normally and are phenotypically unremarkable. Activated naive CD4+ T cells from these mice fail to produce IL-2 and do not proliferate well (Sabapathy, K, Hu, Y, Kallunki, T, Schreiber, M, David, J-P, Jochum, W, Wagner, E, Karin, M. *Curr Biol* 9: 116-125, 1999). It is possible to induce T cell differentiation in T cells from these mice, generating Th1 cells (producers of IFN-g and TNFβ and Th2 effector cells (producers of IL-4, IL-5, IL-6, IL-10 and IL-13) [22,23]. Deletion of either JNK1 or JNK2 in mice resulted in a selective defect in the ability of Th 1 effector cells to express IFNg. This suggests that JNK1 and JNK2 do not have redundant functions in T cells and that they play different roles in the , control of cell growth, differentiation and death. The JNK pathway therefore, is an important point for regulation of T cell responses to antigen.

Cardiovascular disease (CVD) accounts for nearly one quarter of total annual deaths worldwide. Vascular disorders such as atherosclerosis and restenosis result from dysregulated growth of the vessel wall, restricting blood flow to vital organs. The JNK pathway is activated by atherogenic stimuli and regulates local cytokine and growth factor production in vascular cells (Yang, D D, Conze, D, Whitmarsh, A J, et al, *Immunity*, 9:575, 1998). In addition, alterations in blood flow, hemodynamic forces and blood volume lead to JNK activation in vascular endothelium, leading to AP-1 activation and pro-atherosclerotic gene expression (Aspenstrom P., Lindberg U., and Hall A. *Curr. Biol.* 6:7077, 1996). Ischemia and ischemia coupled with reperfusion in the heart, kidney or brain results in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. The JNK pathway is activated by ischemia and reperfusion (Li Y., Shyy J., Li S., Lee J., Su B., Karin M., Chien S *Mol. Cell. Biol.* 16:5947-5954, 1996), leading to the activation of JNK-responsive genes and leukocyte-mediated tissue damage. In a number of different settings JNK activation can be either pro- or anti-apoptotic. JNK activation is correlated with enhanced apoptosis in cardiac tissues following ischemia and reperfusion (Pombo C M, Bonventre J V, Avruch J, Woodgett J R, Kyriakis J. M, Force T. *J. Biol. Chem.* 269:26546-26551, 1994).

Cancer is characterized by uncontrolled growth, proliferation and migration of cells. Cancer is the second leading cause of death with 500,000 deaths and an estimated 1.3 million new cases in the United States in 1996. The role of signal transduction pathways contributing to cell transformation and cancer is a generally accepted concept. The JNK pathway leading to AP-1 appears to play a critical role in cancer. Expression of c-jun is altered in early lung cancer and may mediate growth factor signaling in non-small cell lung cancer (Yin T., Sandhu G., Wolfgang C. D., Burner A., Webb R. L., Rigel D. F. Hai T., and Whelan J. *J. Biol. Chem.* 272:19943-19950, 1997). Indeed, over-expression of c-jun in cells results in transformation, and blocking c-jun activity inhibits MCF-7 colony formation (Szabo E., Riffe M., Steinberg S. M., Birrer M. J., Linnoila R. I. *Cancer Res.* 56:305-315, 1996). DNA-damaging agents, ionizing radiation and tumor necrosis factor activate the JNK pathway. In addition to regulating c-jun production and activity, JNK activation can regulate phosphorylation of p53, and thus can modulate cell cycle progression (Chen T. K., Smith L. M., Gebhardt D. K., Birrer M. J., Brown P. H. *Mol. Carcinogenesis* 15:215-226, 1996). The Oncogene BCR-Ab1, associated with t(9,22) Philadelphia chromosome translocation of chronic myelogenous leukemia, activates JNK and leads to transformation of hematopoietic cells (Milne D. M., Campbell L. E., Campbell D. G., Meek D. W. *J. Biol. Chem.* 270:5511-5518, 1995). Selective inhibition of JNK activation by a naturally occurring JNK inhibitory protein, called JIP-1, blocks cellular transformation caused by BCR-Ab1 expression (Raitano A. B., Halpern J. R., Hambuch T. M., Sawyers C. L. *Proc. Nat. Acad. Sci. USA* 92:11746-11750, 1995). Thus, JNK inhibitors may block transformation and tumor cell growth.

The involvement of JNK in insulin mediated diseases such as Type II diabetes and obesity has also been confirmed (Hirosumi, J. et al *Nature* 420:333-336, 2002; International Publication No. WO 02/085396). Without being limited by theory, it is thought that phosphorylation at Ser 307 of insulin receptor substrate ("IRS-1") is responsible for TNF-α-induced and FFA-induced insulin resistance (Hotamisigil, G. H. *Science* 271:665-668, 1996). This was demonstrated in a cellular model of insulin resistance in liver cells where increased Ser 307 phosphorylation of IRS-1 was seen in cells treated with TNF-α (Hirosumi, J. Id.). It was also shown that the TNF-α-induced Ser 307 phosphorylation was completely prevented by Compound 1 of the present invention (Id.). Additional studies have demonstrated that inhibition of the JNK pathway inhibits TNF-α lipolysis which has been implicated in diseases characterized by insulin resistance (International Publication No. WO 99/53927).

Accordingly, there is a need in the art for inhibitors of JNK, as well as for methods for preparation thereof, pharmaceutical compositions comprising such inhibitors, and methods of inhibiting JNK's and treating diseases in mammals which are responsive to JNK inhibition. The present invention fulfills these needs, and provides further related advantages.

Citation of any reference in Section 2 of this application is not an admission that the reference is prior art to the application.

SUMMARY OF THE INVENTION

In brief, the present invention relates to methods for treating or preventing a disease or disorder, comprising administering to a patient in need thereof an effective amount of a compound having the following formula (I):

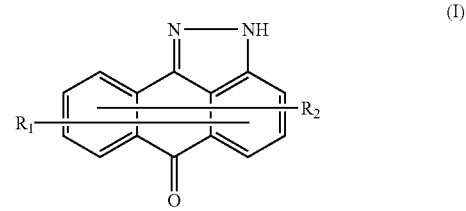

and pharmaceutically acceptable salts thereof, wherein $R_1$ and $R_2$ are as defined below.

A compound of formula (I), or a pharmaceutically acceptable salt thereof, is hereinafter referred to as a "Pyrazoloanthrone Derivative."

Pyrazoloanthrone Derivatives are useful for treating or preventing an inflammatory condition including, but not limited to: diabetes (such as Type II diabetes, Type I diabetes, diabetes insipidus, diabetes mellitus, maturity-onset diabetes, juvenile diabetes, insulin-dependant diabetes, non-insulin dependant diabetes, malnutrition-related diabetes, ketosis-prone diabetes or ketosis-resistant diabetes); nephropathy (such as glomerulonephritis or acute/chronic kidney failure); obesity (such as hereditary obesity, dietary obesity, hormone related obesity or obesity related to the administration of medication); hearing loss (such as that from otitis externa or acute otitis media); fibrosis related diseases (such as pulmonary interstitial fibrosis, renal fibrosis, cystic fibrosis, liver fibrosis, wound-healing or burn-healing, wherein the burn is a first-, second- or third-degree burn and/or a thermal, chemical or electrical burn); arthritis (such as rheumatoid arthritis, rheumatoid spondylitis, osteoarthritis or gout); an allergy; allergic rhinitis; acute respiratory distress syndrome; asthma; bronchitis; an inflammatory bowel disease (such as irritable bowel syndrome, mucous colitis, ulcerative colitis, Crohn's disease, gastritis, esophagitis, pancreatitis or peritonitis); or an autoimmune disease (such as scleroderma, systemic lupus erythematosus, myasthenia gravis, transplant rejection, endotoxin shock, sepsis, psoriasis, eczema, dermatitis or multiple sclerosis).

Pyrazoloanthrone Derivatives are also useful for treating or preventing a liver disease (such as hepatitis, alcohol-induced liver disease, toxin-induced liver disease, steatosis or sclerosis); a cardiovascular disease (such as atherosclerosis, restenosis following angioplasty, left ventricular hypertrophy, myocardial infarction, chronic obstructive pulmonary disease or stroke); ischemic damage (such as to the heart, kidney, liver or brain); ischemia-reperfusion injury (such as that caused by transplant, surgical trauma, hypotension, thrombosis or trauma injury); neurodegenerative disease (such as epilepsy, Alzheimer's disease, Huntington's disease, Amyotrophic laterial sclerosis, peripheral neuropathies, spinal cord damage or Parkinson's disease); or cancer (such as cancer of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system).

In one embodiment, the present methods for treating or preventing further comprise the administration of an effective amount of another therapeutic agent useful for treating or preventing the diseases or disorders disclosed herein. In this embodiment, the time in which the therapeutic effect of the other therapeutic agent is exerted overlaps with the time in which the therapeutic effect of the Pyrazoloanthrone Derivative is exerted.

These and other aspects of this invention will be apparent upon reference to the following detailed description. To that end, certain patent and other documents are cited herein to more specifically set forth various aspects of this invention. Each of these documents are hereby incorporated by reference in their entirety.

DETAILED DESCRIPTION OF THE INVENTION

Definitions

Figure 1:
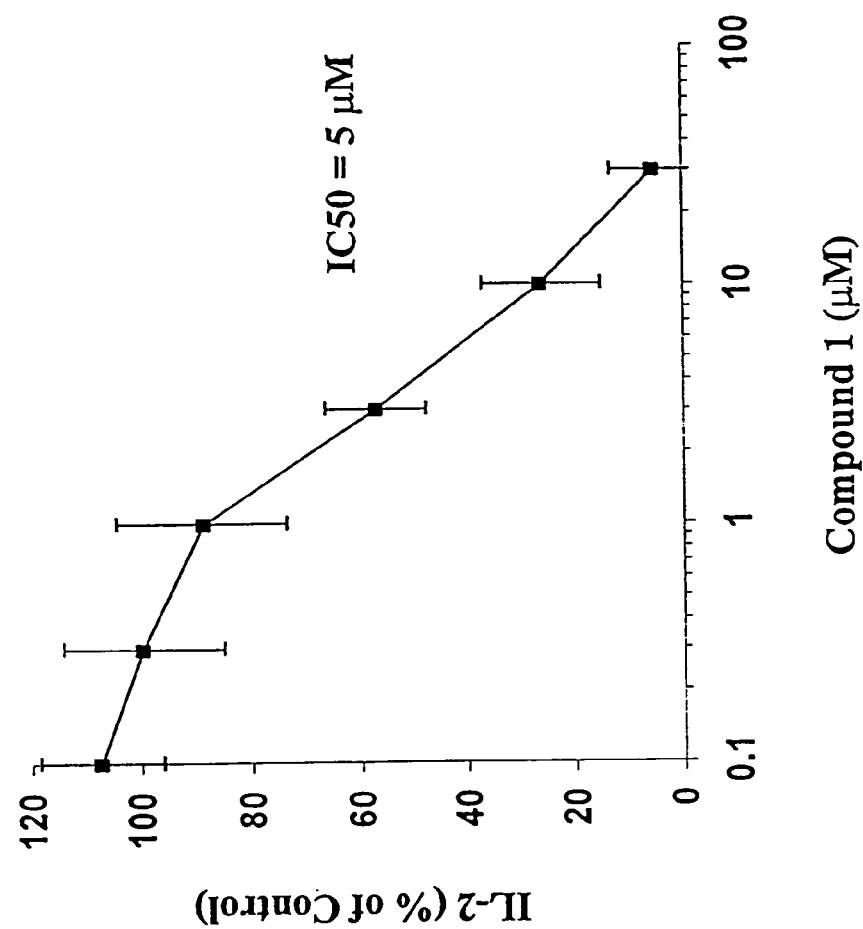
FIG. 1 illustrates the ability of a representative compound of this invention to inhibit IL-2 in Jurkat T-Cell.

As used herein, the terms used above having following meaning.

"Alkyl" means a straight chain or branched, saturated or unsaturated alkyl, cyclic or non-cyclic hydrocarbon having from 1 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Unsaturated alkyls contain at least one double or triple bond between adjacent carbon atoms (also referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cycloalkyls are also referred to herein as "carbocyclic" rings systems, and include bi- and tri-cyclic ring systems having from 8 to 14 carbon atoms such as a cycloalkyl (such as cyclopentane or cyclohexane) fused to one or more aromatic (such as phenyl) or non-aromatic (such as cyclohexane) carbocyclic rings.

"Halogen" means fluorine, chlorine, bromine or iodine.

"Trifluoromethyl" means —$CF_3$.

"Sulfonyl" means —$SO_3$.

"Carboxyl" means —COOH.

"Alkoxy" means —O-(alkyl), such as methoxy, ethoxy, n-propyloxy, isopropyloxy, n-butyloxy, iso-butyloxy, and the like.

"Alkoxyalkoxy" means —O-(alkyl)-O-(alkyl), such as —$OCH_2CH_2OCH_3$, and the like.

"Alkoxycarbonyl" means —C(=O)O-(alkyl), such as —C(=O)$OCH_3$, —C(=O)$OCH_2CH_3$, and the like.

"Alkoxyalkyl" means —(alkyl)-O-(alkyl), such as —$CH_2OCH_3$, —$CH_2OCH_2CH_3$, and the like.

"Aryl" means a carbocyclic or heterocyclic aromatic group containing from 5 to 10 ring atoms. The ring atoms of a carbocyclic aryl group are all carbon atoms, and includes phenyl and naphthyl. The ring atoms of a heterocyclic aryl group contains at least one heteroatom selected from nitrogen, oxygen and sulfur, and include pyridinyl, pyrimidinyl, furanyl, thienyl, imidazolyl, thiazolyl, pyrazolyl, pyridazinyl, pyrazinyl, triazinyl, tetrazolyl, and indolyl.

"Aryloxy" means —O-(aryl), such as —O-phenyl, —O-pyridinyl, and the like.

"Arylalkyl" means —(alkyl)-(aryl), such as benzyl (i.e., —CH$_2$phenyl), —CH$_2$-pyridinyl, and the like.

"Arylalkyloxy" means —O-(alkyl)-(aryl), such as —O-benzyl, —O—CH$_2$-pyridinyl, and the like.

"Cycloalkyl" means a cyclic alkyl having from 3 to 7 carbon atoms, such as cyclopropyl, cyclopentyl, cyclohexyl, and the like.

"Cycloalkyloxy" means —O-(cycloalkyl), such as —O-cyclohexyl, and the like.

"Cycloalkylalkyloxy" means —O-(alkyl)-(cycloalkyl), such as —OCH$_2$cyclohexyl, and the like.

"Alkylidene" means the divalent radical —C$_n$H$_{2n}$—, wherein n is an integer from 1 to 8, such as —CH$_2$—, —CH$_2$CH$_2$—, —CH$_2$—CH$_2$—CH$_2$—, —CH$_2$CH$_2$CH$_2$CH$_2$—, —CH$_2$CH$_2$CH$_2$CH$_2$CH$_2$—, and the like.

"Heteroatom-containing alkylidene" means an alkylidene wherein at least one carbon atom is replaced by a heteroatom selected from nitrogen, oxygen or sulfur, such as —CH$_2$CH$_2$OCH$_2$CH$_2$—, and the like.

"Aminoalkoxy" means —O-(alkyl)-NH$_2$, such as —OCH$_2$NH$_2$, —OCH$_2$CH$_2$NH$_2$, and the like.

"Mono- or di-alkylamino" means —NH(alkyl) or —N(alkyl)(alkyl), respectively, such as —NHCH$_3$, —N(CH$_3$)$_2$, and the like.

"Mono- or di-alkylaminoalkoxy" means —O-(alkyl)-NH(alkyl) or —O-(alkyl)N(alkyl)(alkyl), respectively, such as —OCH$_2$NHCH$_3$, —OCH$_2$CH$_2$N(CH$_3$)$_2$, and the like.

"Arylamino" means —NH(aryl), such as —NH-phenyl, —NH-pyridinyl, and the like.

"Arylalkylamino" means —NH-(alkyl)-(aryl), such as —NH-benzyl, —NHCH$_2$pyridinyl, and the like.

"Alkylamino" means —NH(alkyl), such as —NHCH$_3$, —NHCH$_2$CH$_3$, and the like.

"Cycloalkylamino" means —NH-(cycloalkyl), such as —NH-cyclohexyl, and the like.

"Cycloalkylalkylamino" —NH-(alkyl)-(cycloalkyl), such as —NHCH$_2$-cyclohexyl, and the like.

An "effective amount" when used in connection with a Pyrazoloanthrone Derivative is an amount effective for treating or preventing an inflammatory condition, a liver disease, a cardiovascular disease, a neurodegenerative disease or cancer.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In certain embodiments, the patient is an infant, child, adolescent or adult.

Compounds of the Invention

As mentioned above, the present invention is related to methods for treating or preventing an inflammatory condition, a liver disease, a cardiovascular disease, a neurodegenerative disease or cancer, comprising administering to a patient in need thereof an effective amount of a Pyrazoloanthrone Derivative of formula (I):

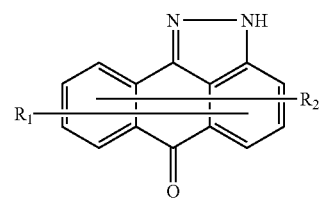

wherein:

R$^1$ and R$_2$ are optional substituents that are the same or different and independently represent alkyl, halogen, nitro, trifluoromethyl, sulfonyl, carboxyl, alkoxycarbonyl, alkoxy, aryl, aryloxy, arylalkyloxy, arylalkyl, cycloalkylalkyloxy, cycloalkyloxy, alkoxyalkyl, alkoxyalkoxy, aminoalkoxy, mono- or di-alkylaminoalkoxy, or a group represented by formula (a), (b), (c) or (d):

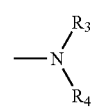
(a)

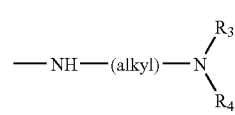
(b)

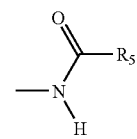
(c)

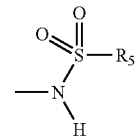
(d)

R$_3$ and R$_4$ taken together represent alkylidene or a heteroatom-containing alkylidene, or R$_3$ and R$_4$ are the same or different and independently represent hydrogen, alkyl, cycloalkyl, aryl, arylalkyl, cycloalkylalkyl, aryloxyalkyl, alkoxyalkyl, alkoxyamino, or alkoxy(mono- or di-alkylamino); and R$_5$ represents hydrogen, alkyl, cycloalkyl, aryl, arylalkyl, cycloalkylalkyl, alkoxy, amino, mono- or di-alkylamino, arylamino, arylalkylamino, cycloalkylamino, or cycloalkylalkylamino.

In the embodiment wherein R$_1$ and R$_2$ are not present, Pyrazoloanthrone Derivatives have the following structure (II) (also referred to herein as "Compound I"):

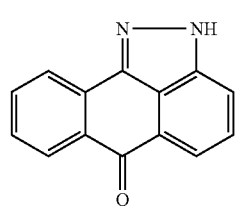

This compound is commercially available from Pfaltz-Bauer (Conn., U.S.).

In the embodiment wherein only one of $R_1$ and $R_2$ is present, Pyrazoloanthrone Derivatives have one of the following structures (III) or (IV):

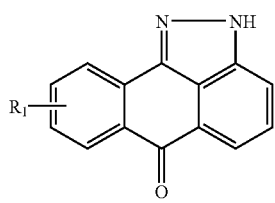

(III)

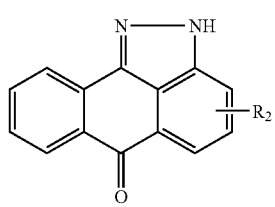

(IV)

In the embodiment wherein both $R_1$ and $R_2$ are present, Pyrazoloanthrone Derivatives have one of the following structures (V), (VI) or (VII):

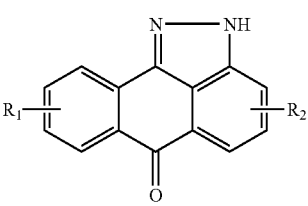

(V)

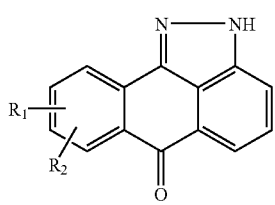

(VI)

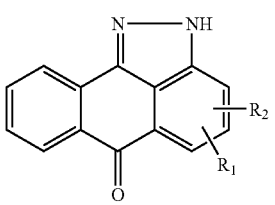

(VII)

A Pyrazoloanthrone Derivative can be in the form of a pharmaceutically acceptable salt or a free base. Pharmaceutically acceptable salts of the Pyrazoloanthrone Derivatives can be formed from organic and inorganic acids. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. The compounds may also be used in the form of base addition salts. Suitable pharmaceutically acceptable base addition salts for the compound of the present invention include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995). Thus, the term "pharmaceutically acceptable salt" of a compound of formula (I) is intended to encompass any and all acceptable salt forms.

Preparation of Compounds of the Invention

The Pyrazoloanthrone Derivatives can be made using organic synthesis techniques known to those skilled in the art, as well as by the following general techniques and by the procedures set forth in the Examples. To that end, the Pyrazoloanthrone Derivatives can be made according to the following Reaction Schemes 1 through 7.

Reaction Scheme 1

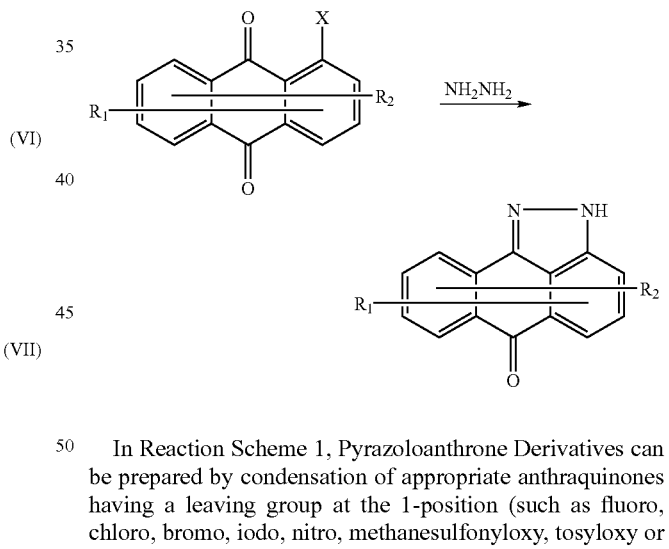

In Reaction Scheme 1, Pyrazoloanthrone Derivatives can be prepared by condensation of appropriate anthraquinones having a leaving group at the 1-position (such as fluoro, chloro, bromo, iodo, nitro, methanesulfonyloxy, tosyloxy or phenoxy) with hydrazine in a suitable solvent (such as pyridine, dimethylformamide, methylene chloride, chloroform, or dioxane). The reaction is carried out at temperatures ranging 0° C. to 200° C. for 1 to 16 hours. Suitable anthraquinone starting materials are commercially available from a variety of sources with the $R_1$ and/or $R_2$ groups at various positions on the anthraquinone ring. For purpose of illustration, the following reaction schemes depict synthesis of 5- and/or 7-substituted Pyrazoloanthrone Derivatives. One skilled in the art will recognize that Pyrazoloanthrone Derivatives substituted at other positions may be made in a similar manner from the appropriately substituted pyrazoloanthrone starting material.

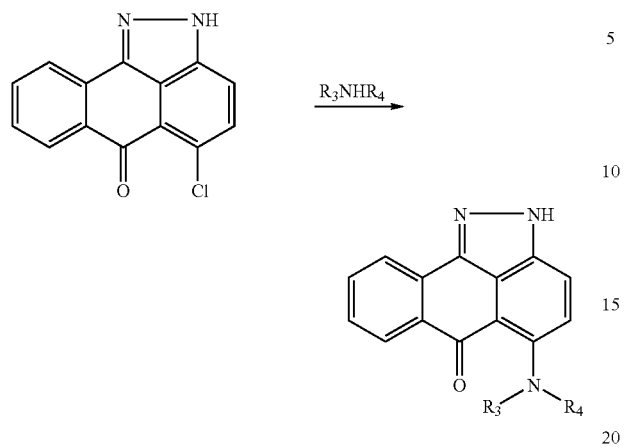

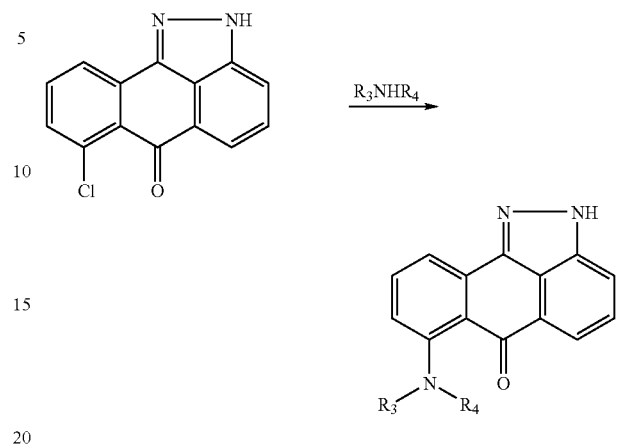

In Reaction Scheme 2, Pyrazoloanthrone Derivatives with 5-amino substituents can be prepared by condensation of 5-chloropyrazoloanthrone with mono- or disubstituted amines at 0 to 250° C. for 1 to 16 hours, either in the absence or the presence of a solvent. Typically solvents are pyridine, dimethylformamide, dimethylsulfoxide, dichloroethane, chloroform, tetrahydrofuran, dioxane, diglyme, or triglyme in the presence of excess amount of the amine, or in the presence of an acid quenching agent such as triethylamine, diisopropylethylamine, sodium bicarbonate, potassium carbonate, or sodium hydroxide.

In Reaction Scheme 3, Pyrazoloanthrone Derivatives with 7-amino substituents can be prepared by condensation of 7-chloropyrazoloanthrone with mono- or disubstituted amines at 0 to 250° C. for 1 to 16 hours either in the absence or the presence of a solvent. Typically solvents are pyridine, dimethylformamide, dimethylsulfoxide, dichloroethane, chloroform, tetrahydrofuran, dioxane, diglyme, or triglyme in the presence of excess amount of the amine, or in the presence of an acid quenching agent such as triethylamine, diisopropylethylamine, sodium bicarbonate, potassium carbonate, or sodium hydroxide.

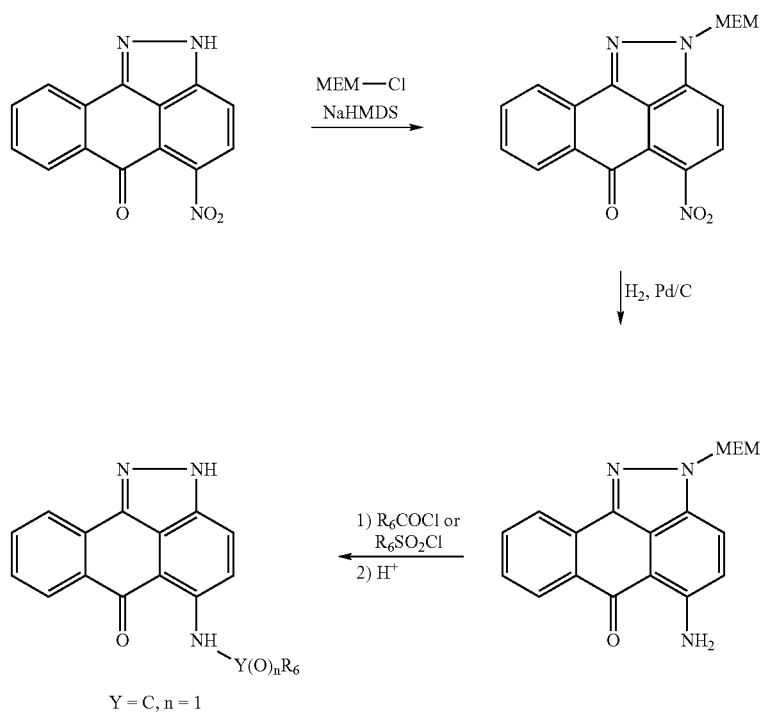

In Reaction Scheme 4, Pyrazoloanthrone Derivatives with 5-acyl- or sulfonylamino substituents can be prepared by condensation of 5-amino-2-(2methoxyethoxymethyl) pyrazoloanthrone with acid chlorides and sulfonyl chlorides followed by deprotection. Condensation of 5-amino-2-(2-methoxyethoxymethyl) pyrazoloanthrone with appropriate acid chlorides $R_6COCl$ or sulfonyl chlorides $R_6SO_2Cl$ is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, and ethyl acetate. The deprotection step may be performed by the treatment of the product mentioned above with an acid such as trifluoroacetic acid, aqueous hydrochloric acid, aqueous hydrobromic acid, or aqueous sulfuric acid.

The starting material may be prepared in two steps. The 2-position of 5-nitropyrazoloanthrone may be protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N,N-Dimethylamino)pyridine (DMAP) may be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 5-nitropyrazoloanthorone is then reduced to its 5-amino derivative by a variety of reducing agents such as Sn or Fe metal in acidic media such as acetic acid or aqueous hydrochloric acid. The reaction is typically run at 20 to 160° C. for 1 to 16 hours. The same transformation can be carried out by hydrogenation in the presence of a transition-metal catalyst such as palladium, platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 5

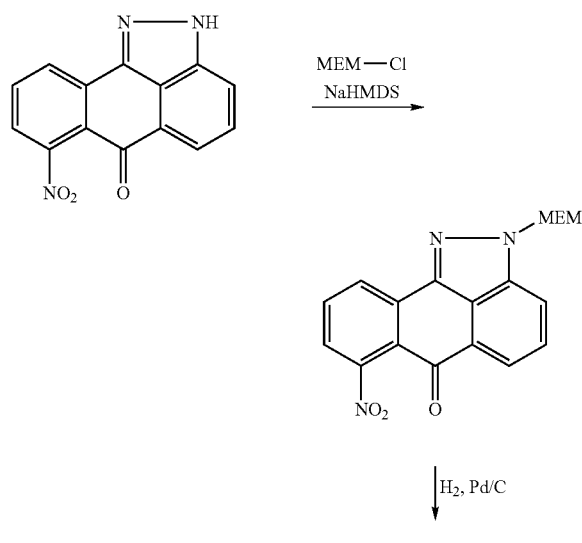

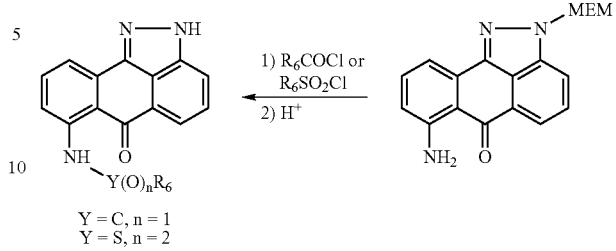

In Reaction Scheme 5, Pyrazoloanthrone Derivatives with 7-acyl- or sulfonylamino substituents can be prepared by condensation of 7-amino-2-(2-methoxyethoxymethyl) pyrazoloanthrone with acid chlorides and sulfonyl chlorides followed by the deprotection. Condensation of 7-amino-2-(2-methoxyethoxymethyl)pyrazoloanthrone with appropriate acid chlorides $R_6COCl$ or sulfonyl chlorides $R_6SO_2Cl$ is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, or ethyl acetate. The deprotection step may be performed by the treatment of the product mentioned above with an acid such as trifluoroacetic acid, aqueous hydrochloric acid, aqueous hydrobromic acid or aqueous sulfuric acid.

The starting material is prepared in two steps. The 2-position of 7-nitropyrazoloanthrone is protected by a protective group such as methoxymethyl (MOM) methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N,N-dimethylamino)pyridine (DMAP) can be used as a catalyst when a tertiary amine is use as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 7-nitropyrazoloanthorone is then reduced to its 7-amine derivative by a variety of reducing agents such as Sn or Fe metal in acidic media such a acetic acid or aqueous hydrochloric acid. The reaction is typically run at 20 to 160° C. for 5 to 16 hours. The same transformation can be carried out by hydrogenation in the presence of a transition-metal catalyst such as palladium, platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 6

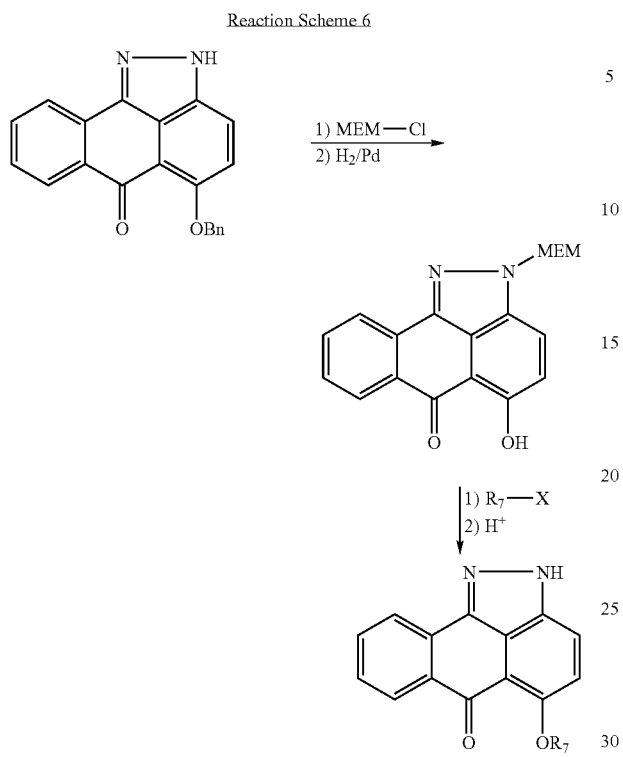

In Reaction Scheme 6, Pyrazoloanthrone Derivatives with 5-alkoxy substituents can be prepared by condensation of 5-hydroxy-2-(2-methoxyethoxymethyl)pyrazoloanthrone with alkyl halides and sulfonates $R_7$—X followed by deprotection. As the leaving group X, chloride, bromide, iodide, methanesulfonate, tosylate, benzenesulfonate, or triflate can be used. Condensation of 5-hydroxy-2-(2-methoxyethoxymethyl) pyrazoloanthrone with appropriate alkyl halides and sulfonates is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, or ethyl acetate. The deprotection step is performed by the treatment of the product mentioned above with an acid such as trifluoroacetic acid, aqueous hydrochloric acid, aqueous hydrobromic acid, or aqueous sulfuric acid.

The starting material is prepared in two steps. The 2-position of 5-benzyloxypyrazoloanthrone is protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N,N-dimethylamino) pyridine (DMAP) can be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 5-benzyloxypyrazoloanthorone is then reduced to its 5-hydroxy derivative by hydrogenation in the presence of a transition-metal catalyst, such as palladium platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Reaction Scheme 7

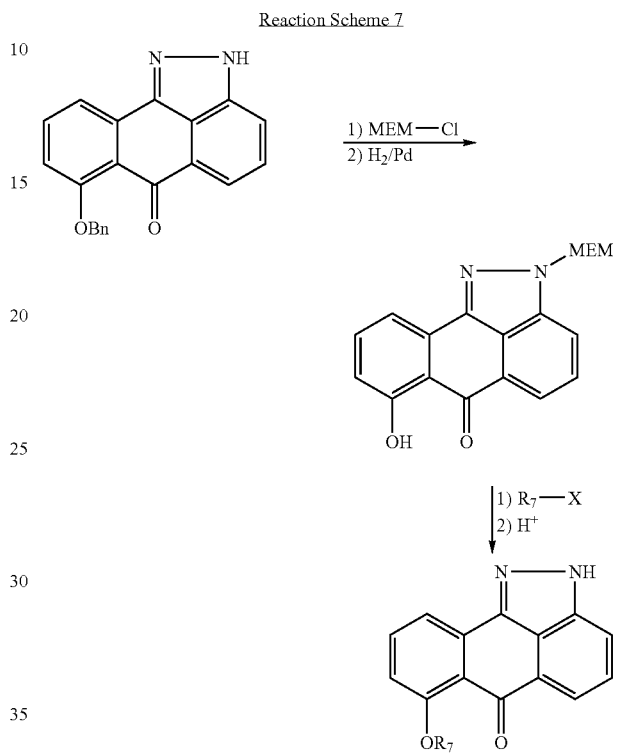

In Reaction Scheme 7, Pyrazoloanthrone Derivatives with 5-alkoxy substituents can be prepared by condensation of 7-hydroxy-2-(2-methoxyethoxymethyl)pyrazoloanthrone with alkyl halides and sulfonates $R_7$—X followed by deprotection. As the leaving group X, chloride, bromide, iodide, methanesulfonate, tosylate, benzenesulfonate, or triflate can be used. Condensation of 7-hydroxy-2-(2-methoxyethoxymethyl) pyrazoloanthrone with appropriate alkyl halides and sulfonates is carried out in the presence of an acid quenching agent such as triethylamine, diisopropylethylamine, sodium bicarbonate, potassium carbonate, or sodium hydroxide at −20 to 50° C. for 0.5 to 16 hours in solvents such as methylene chloride, chloroform, tetrahydrofuran, dioxane, dimethylformamide, or ethyl acetate. The deprotection step is performed by the treatment of the product mentioned above with an acid such as trifluoroacetic acid, aqueous hydrochloric acid, aqueous hydrobromic acid, or aqueous sulfuric acid.

The starting material is prepared in two steps. The 2-position of 7-benzyloxypyrazoloanthrone is protected by a protective group such as methoxymethyl (MOM), methoxyethoxymethyl (MEM), 2-trimethylsilylethoxymethyl (SEM), or 4-methoxybenzyl (PMB) with an aid of a base such as triethylamine, diisopropylethylamine, pyridine, sodium hexamethyldisilazide, potassium hexamethyldisilazide, or lithium diisopropylamide. 4-(N,N-dimethylamino) pyridine (DMAP) can be used as a catalyst when a tertiary amine is used as a base. The reaction is typically carried out at −40 to 60° C. for 1 to 16 hours in a solvent such as methylene chloride, chloroform, tetrahydrofuran, dioxane, or dimethoxyethane. As the nitrogen protective group, MEM group is preferred.

N-Protected 7-benzyloxypyrazoloanthorone is then reduced to its 7-hydroxy derivative by hydrogenation in the presence of a transition-metal catalyst, such as palladium platinum, rhodium, or iridium with or without a support such as charcoal in a solvent such as ethanol, ethyl acetate, tetrahydrofuran, dioxane, or dimethoxyethane at 1 to 20 atmospheres of hydrogen at 20 to 60° C. for 1 to 16 hours. The procedure using hydrogenation with palladium on charcoal as the catalyst is preferred.

Pyrazoloanthrone Derivatives of structures (V), (VI) and (VII) can be made by the same procedures as outlined above by utilizing starting materials having multiple reactive sites at the corresponding positions to the desired product.

Methods of Use

The present invention provides methods for treating or preventing a variety of conditions comprising administering an effective amount of a Pyrazoloanthrone Derivative to a patient in need thereof. Conditions that may be treated by the administration of the Pyrazoloanthrone Derivatives, include any condition which is responsive to JNK inhibition, and thereby benefits from administration of a JNK inhibitor. Representative conditions treatable or preventable by administering an effective amount of a Pyrazoloanthrone Derivatives are useful for treating or preventing an inflammatory condition including, but not limited to: diabetes (such as Type II diabetes, Type I diabetes, diabetes insipidus, diabetes mellitus, maturity-onset diabetes, juvenile diabetes, insulin-dependant diabetes, non-insulin dependant diabetes, malnutrition-related diabetes, ketosis-prone diabetes or ketosis-resistant diabetes); nephropathy (such as glomerulonephritis or acute/chronic kidney failure); obesity (such as hereditary obesity, dietary obesity, hormone related obesity or obesity related to the administration of medication); hearing loss (such as that from otitis externa or acute otitis media); fibrosis related diseases (such as pulmonary interstitial fibrosis, renal fibrosis, cystic fibrosis, liver fibrosis, wound-healing or burn-healing, wherein the burn is a first-, second- or third-degree burn and/or a thermal, chemical or electrical burn); arthritis (such as rheumatoid arthritis, rheumatoid spondylitis, osteoarthritis or gout); an allergy; allergic rhinitis; acute respiratory distress syndrome; asthma; bronchitis; an inflammatory bowel disease (such as irritable bowel syndrome, mucous colitis, ulcerative colitis, Crohn's disease, gastritis, esophagitis, pancreatitis or peritonitis); or an autoimmune disease (such as scleroderma, systemic lupus erythematosus, myasthenia gravis, transplant rejection, endotoxin shock, sepsis, psoriasis, eczema, dermatitis or multiple sclerosis).

Pyrazoloanthrone Derivatives are also useful for treating or preventing a liver disease (such as hepatitis, alcohol-induced liver disease, toxin-induced liver disease, steatosis or sclerosis); a cardiovascular disease (such as atherosclerosis, restenosis following angioplasty, left ventricular hypertrophy, myocardial infarction, chronic obstructive pulmonary disease or stroke); ischemic damage (such as to the heart, kidney, liver or brain); ischemia-reperfusion injury (such as that caused by transplant, surgical trauma, hypotension, thrombosis or trauma injury); neurodegenerative disease (such as epilepsy, Alzheimer's disease, Huntington's disease, Amyotrophic laterial sclerosis, peripheral neuropathies, spinal cord damage or Parkinson's disease); or cancer (cancer of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system).

In one embodiment, the present methods for treating or preventing further comprise the administration of an effective amount of another therapeutic agent useful for treating or preventing the diseases or disorders disclosed herein. In this embodiment, the time in which the therapeutic effect of the other therapeutic agent is exerted overlaps with the time in which the therapeutic effect of the Pyrazoloanthrone Derivative is exerted.

In one embodiment, the other therapeutic agent is an anti-inflammatory agent. Examples of anti-inflammatory agents include, but are not limited to, steroids (e.g., cortisol, cortisone, fludrocortisone, prednisone, 6α-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antiobiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

In one embodiment, inhibiting JNK in vivo comprises inhibiting TNF-α in vivo.

In one embodiment the JNK is JNK1. In another embodiment the JNK is JNK2. In another embodiment the JNK is JNK3.

Pharmaceutical Compositions

Pharmaceutical compositions can be used in the preparation of individual, single unit dosage forms. Pharmaceutical compositions and dosage forms of the invention comprise a Pyrazoloanthrone Derivative and one or more excipients.

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels, liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more Pyrazoloanthrone Derivatives than a dosage form used in the chronic treatment of the same disease. Similarly, a parenteral dosage form may contain smaller amounts of a Pyrazoloanthrone Derivative than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active agents in the dosage form. For example, the decomposition of some active agents may be accelerated by some excipients such as lactose, or when exposed to water. Active agents that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active agent.

Lactose-free compositions of the invention can comprise excipients that are well known in the art and are listed, for example, in the *U.S. Pharmacopeia* (USP) 25-NF20 (2002). In general, lactose-free compositions comprise active agents, a binder/filler, and a lubricant in pharmaceutically compatible and pharmaceutically acceptable amounts. Preferred lactose-free dosage forms comprise active agents, microcrystalline cellulose, pre-gelatinized starch, and magnesium stearate.

Anhydrous (less than 5% water) pharmaceutical compositions and dosage forms of the invention can be prepared using anhydrous or low moisture containing agents and low moisture or low humidity conditions. Pharmaceutical compositions and dosage forms that comprise lactose and at least one active agent that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active agent will decompose. Such compounds, which are referred to herein as "stabilizers," include, but are not limited to, antioxidants such as ascorbic acid, pH buffers, or salt buffers.

The amount of a Pyrazoloanthrone Derivative in a dosage form may differ depending on factors such as, but not limited to, the route by which it is to be administered to patients. However, typical dosage forms of the invention comprise a Pyrazoloanthrone Derivative in an amount of from about 0.10 mg to about 3500 mg, from about 1 mg to about 2500 mg, from about 10 mg to about 500 mg, from about 25 mg to about 250 mg, from about 50 mg to about 100 mg. Typical dosage forms comprise a Pyrazoloanthrone Derivative in an amount of about 0.1, 1, 2, 5, 7.5, 10, 12.5, 15, 17.5, 20, 25, 50, 100, 150, 200, 250, 500, 750, 1000, 1500, 2000, 2500, 3000 or 3500 mg. In a particular embodiment, a dosage form comprises a Pyrazoloanthrone Derivative in an amount of about 1, 2, 5, 10, 25, 50, 100, 250 or 500 mg. In a specific embodiment, a dosage form comprises an amount of about 5, 10, 25 or 50 mg of a Pyrazoloanthrone Derivative.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of a Pyrazoloanthrone Derivative, and may be prepared by methods of pharmacy well known to those skilled in the art. 'see generally, *Remington's Pharmaceutical Sciences,* 18th ed., Mack Publishing, Easton Pa. (1990).

Typical oral dosage forms of the invention are prepared by combining a Pyrazoloanthrone Derivative in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the Pyrazoloanthrone Derivative with liquid carriers, finely divided solid carriers, or both, and then shaping the product into the desired presentation if necessary.

For example, a tablet can be prepared by compression or molding. Compressed tablets can be prepared by compressing in a suitable machine the active agents in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103, AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103 and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active agents should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W. R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises a Pyrazoloanthrone Derivative, anhydrous lactose, microcrystalline cellulose, polyvinylpyrrolidone, stearic acid, colloidal anhydrous silica, and gelatin.

Delayed Release Dosage Forms

A JNK Inhibitor can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more Pyrazoloanthrone Derivatives using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with a Pyrazoloanthrone Derivative. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (e.g., a Pyrazoloanthrone Derivative) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active agent can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active agents disclosed herein can also be incorporated into the parenteral dosage forms of the invention. For example, cyclodextrin and its derivatives can be used to increase the solubility of a Pyrazoloanthrone Derivative. See, e.g., U.S. Pat. No. 5,134,127, which is incorporated herein by reference.

Topical and Mucosal Dosage Forms

Topical and mucosal dosage forms of the invention include, but are not limited to, sprays, aerosols, solutions, emulsions, suspensions, or other forms known to one of skill in the art. See, e.g., Remington's Pharmaceutical Sciences, 16$^{th}$ and 18$^{th}$ eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional agents are well known in the art. See, e.g., Remington's Pharmaceutical Sciences, 16$^{th}$ and 18$^{th}$ eds., Mack Publishing, Easton Pa. (1980 & 1990).

The pH of a pharmaceutical composition or dosage form may also be adjusted to improve delivery of one or more active agents. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active agents so as to improve delivery. In this regard, stearates can serve as a lipid vehicle for the formulation, as an emulsifying agent or surfactant, and as a delivery-enhancing or penetration-enhancing agent. Different salts, hydrates or solvates of the active agents can be used to further adjust the properties of the resulting composition.

Kits

Typically, active agents of the invention are preferably not administered to a patient at the same time or by the same route of administration. This invention therefore encompasses kits which, when used by the medical practitioner, can simplify the administration of appropriate amounts of active agents to a patient.

A typical kit of the invention comprises a dosage form of a Pyrazoloanthrone Derivative, or a pharmaceutically acceptable salt salt, solvate, hydrate, stereoisomer, prodrug, or clathrate thereof. Kits encompassed by this invention can further comprise additional active agents. Examples of the additional active agents include, but are not limited to, antidepressants, anticonvulsants, antihypertensives, anxiolytics, calcium channel blockers, muscle relaxants, non-narcotic analgesics, opioid analgesics, non-steroidal anti-inflammatory drugs (NSAIDs), corticosteroids, or other therapeutics discussed herein (see, e.g., section 4.2).

Kits of the invention can further comprise devices that are used to administer the Pyrazoloanthrone Derivative. Examples of such devices include, but are not limited to, syringes, drip bags, patches, and inhalers.

Kits of the invention can further comprise pharmaceutically acceptable vehicles that can be used to administer one or more Pyrazoloanthrone Derivatives. For example, if a Pyrazoloanthrone Derivative is provided in a solid form that must be reconstituted for parenteral administration, the kit can comprise a sealed container of a suitable vehicle in which the a Pyrazoloanthrone Derivative can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, soybean oil, ethyl oleate, isopropyl myristate, and benzyl benzoate.

The following examples are offered by way of illustration, not limitation.

EXAMPLES

Example 1

Synthesis of Representative Compounds

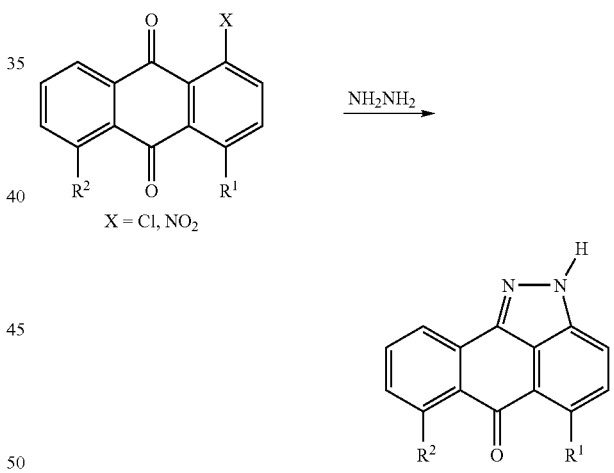

A. Anthra[1,9cd]pyrazol-6(2H)-one ("Compound 1")

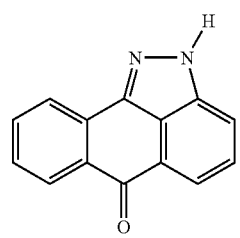

Anhydrous hydrazine is added to a solution of 2-chloroanthraquinone (Aldrich) in 10 mL, pyridine, and the mixture heated at 100° C. for 16 hours. The mixture is cooled and the solvent is evaporated in vacuo. The residue is taken in hot 6N HCl, and the solid is collected by filtration. Flash chromatography of the crude material on silica gel affords anthra[1,9cd]pyrazol-6(2H)-one ("Compound 1") as yellow solids.

Due to limited solubility of Compound 1, purification of the same may be achieved by first derivatizing Compound 1 to a more soluble intermediate, such as the corresponding acetate, recrystallizing the intermediate, and then converting the intermediate to yield purified Compound 1 in good yield. More specifically, to solution of the pyrazoloanthrone (9.67 g, 43.9 mmol) in acetic acid (700 mL) is added acetic anhydride (12.4 mL, 132 mmol). The solution is heated to 80° C. for 5 hours and then cooled to room temperature. After 16 hours, the reaction is cooled to 0° C. for 2 hours. The reaction is then filtered to give the N-acetylpyrazoloanthrone intermediate. This intermediate is recrystallized in acetic acid to give the pure intermediate (5.96 g, 52%). $^1$H NMR (CDCL$_3$) δ 10.6 (br s, 1 H), 8.46 (d, 1 H), 8.33 (d, 1 H), 8.26 (d, 1 H), 8.08 (d, 1 H), 7.96-7.87 (m, 2H), 7.78 (t. 1H), 2.83 (s, 3H); ES-MS (m/z) 263 [M+1]$^+$. To a solution of the pure intermediate, (5.96 g, 23 mmol) in methanol (600 mL) is added ammonium hydroxide (60 mL). The reaction is stirred at room temperature for 16 hours and then filtered and dried in a vacuum oven. A second crop of crystals is recovered to give a total of 4.8 g of Compound 1 at greater than 98% purity. ES-MS (m/z) 221 [M+I]$^{30}$.

B. 5-Chloroanthra[1,9cd]pyrazol-6(2H)-one

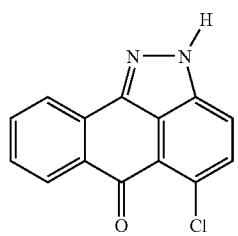

This compound may be made in the same manner from 1,4-dichloroanthraquinone (commercial product).

C. 7-Chloroanthra[1,9cd]pyrazol-6(2H)-oe

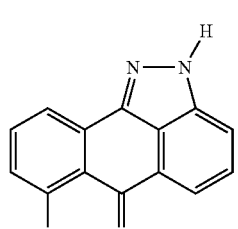

This compound may be made in the same manner from 1,5-dichloroanthraquinone (commercial product).

D. 5-Nitroanthra[1,9cd])pyrazol-6(2H)-one

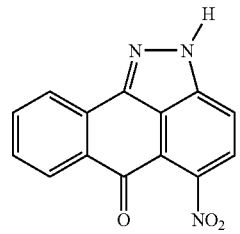

This compound may be made from 1,4-dinitroanthraquinone (Krapcho, A. P.; Avery, K. L., Jr. *J. Org. Chem.* 55, 5562-4, 1990).

E. 7-Nitroanthra[1,9cd]pyrazol-6(2H)-one

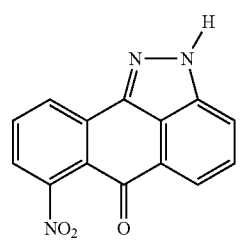

This compound may be made in the same manner from 1-chloroanthraquinone (commercial product).

F. 5-Benzyloxyanthra[1,9cd]pyrazol-6(2H)-one

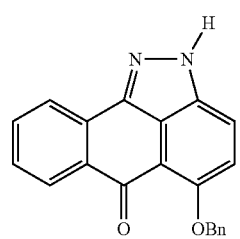

This compound may be made in the same manner from 1-nitro-4-benzyloxyanthraquinone. This starting material may be prepared as follows. Benzyl bromide is added to 1-nitro-4-hydroxyanthraquinone (Aldrich) and potassium carbonate in dimethylformamide, and the mixture is stirred for 16 hours. Water is added and the mixture is extracted with ethyl acetate (×2). The combined organic layer is washed sequentially with sodium bicarbonate solution, water, 1N hydrochloric acid, and brine, dried, and evaporated. The residue is chromatographed on silica gel to afford 1-nitro-4-benzyloxyanthraquinone.

G. 7-Benzyloxyanthra[1,9cd]pyrazol-6(2H)-one

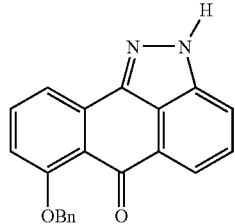

This compound maybe made in the same manner from 1-nitro-5-benzyloxyanthraquinone, which starting material may prepared as disclosed in German Patent No. DE 2254199 to Reubke, Hohmann and Bien.

H. 5-(Acetylamino)anthra[1,9cd]pyrazol-6(2H)-one

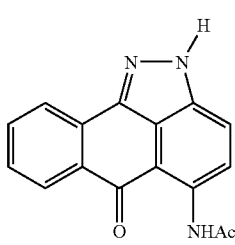

This compound may be made in the same manner from 4-acetylamino-1-chloroanthraquinone. This starting material may be prepared as follows. 4-Amino-1-chloroanthraquinone is taken in pyridine and treated with acetic anhydride. The mixture is stirred for 1 hour, and poured onto water: The solids are collected by filtration, washed with water, and dried in vacuo to give 4-acetylamino-1-chloroanthraquinone as a colorless solid.

Example 2

Synthesis of Representative Compounds

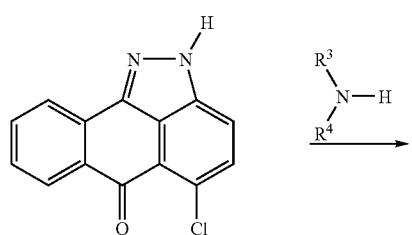

-continued

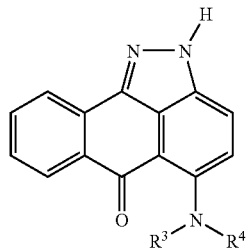

A. 5-(Dimethylamino)anthra[1,9cd]pyrazol-6(2H)-one

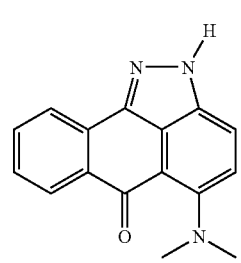

A mixture of 5-chloroanthra[1,9cd]pyrazol-6(2H)-one (Example 1-B) and dimethylamine in pyridine is heated at 100° C. for 16 hours. The mixture is cooled and evaporated. The residue is chromatographed on silica gel to give the desired compound as yellow solids.

B. 5-(1-Piperidinyl)anthra[1,9cd]pyrazol-6(2H)-one

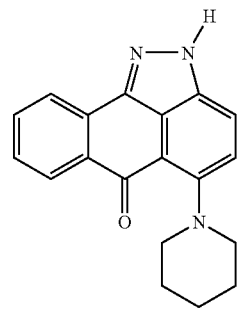

This compound may be made in the same manner using piperidine as the amine.

C. 5-(1-Morpholinyl)anthra[1,9cd]pyrazol-6(2H)-one

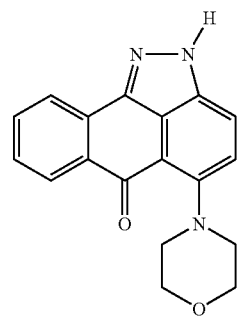

This compound may be made in the same manner using morpholine as the amine.

D. 5-(Benzylamino)anthra[1,9cd]pyrazol-6(2H)-e

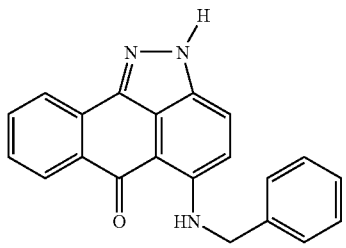

This compound may be made in the same manner using benzylamine as the amine.

E. 5-{(4-Pyridylmethyl)amino}anthra[1,9cd]pyrazol-6(2H)-one

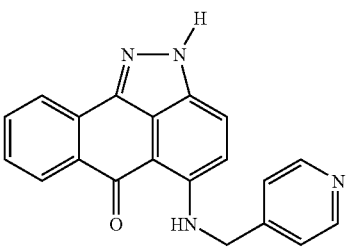

This compound may be made in the same manner using 4-pyridylmethylamine as the amine.

F. 5-{2-(1-Piperidinyl)ethylamino}anthra[1,9cd]pyrazol-6(2H)-one

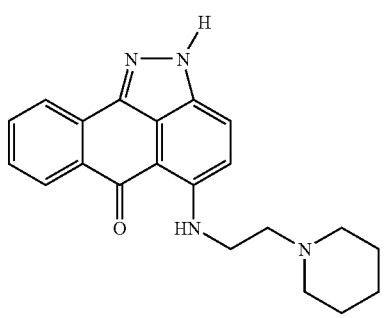

This compound may be made in the same manner using 2-(1-piperidyl)ethylamine as the amine.

Example 3

Synthesis of Representative Compounds

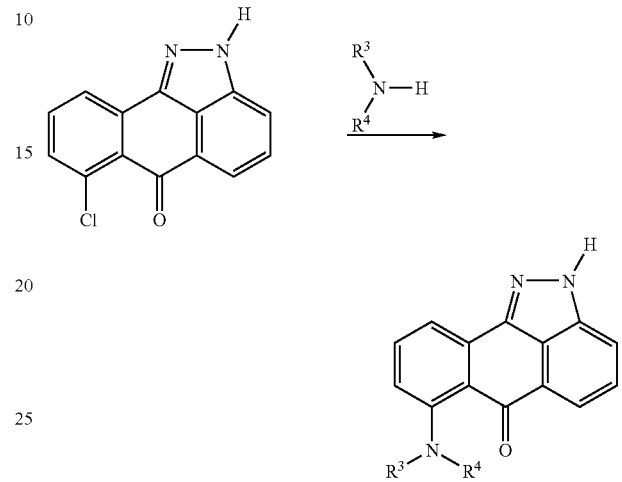

A. 7-(Dimethylamino)anthra[1,9cd]pyrazol-6(2H)-one

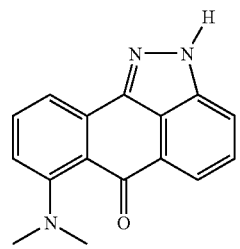

A mixture of 6-chloroanthra[1,9cd]pyrazol-6(2H)-one (Example 1-C) and dimethylamine in pyridine is heated at 100° C. for 16 hours. The mixture is cooled and evaporated. The residue is chromatographed on silica gel to give the desired compound as yellow solids.

B. 5-(1-Piperidinyl)anthra[1,9cd]pyrazol-6(2H)-one

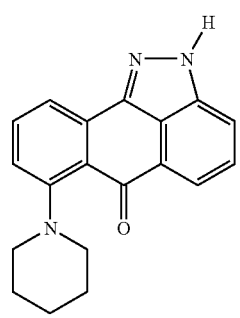

This compound may be made in the same manner using piperidine as the amine.

C. 5-(1-Morpholinyl)anthra[1,9cd]pyrazol-6(2H)-one

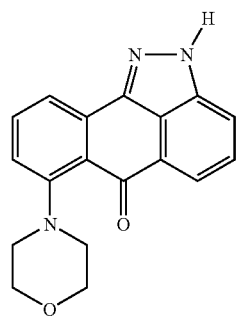

This compound may be made in the same manner using morpholine as the amine.

D. 5-(Benzylamino)anthra[1,9cd]pyrazol-6(2H)-one

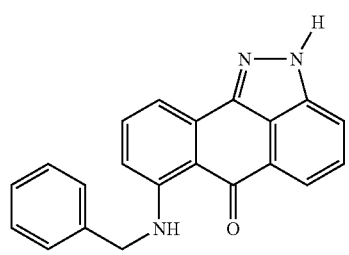

This compound may be made in the same manner using benzylamine as the amine.

E. 5-{(4-Pyridylmethyl)amino}anthra[1,9cd]pyrazol-6(2H)-one

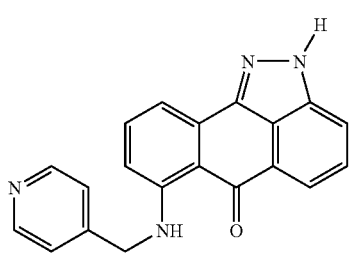

This compound may be made in the same manner using 4-pyridylmethylamine as the amine.

F. 5-{2-(1-Piperidinyl)ethylamino}anthra[1,9cd]pyrazol-6(2H)-one

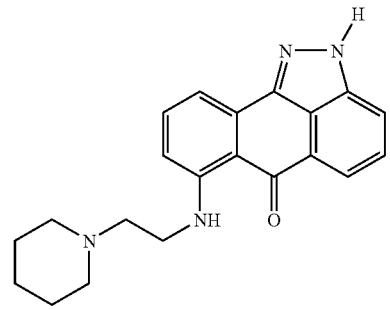

This compound may be made in the same manner using 2-(1-piperidyl)ethylamine as the amine.

Example 4

Synthesis of Representative Compounds

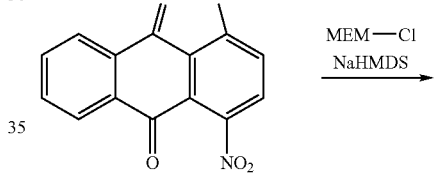

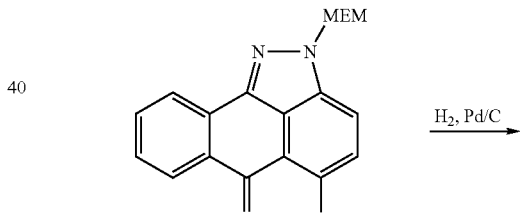

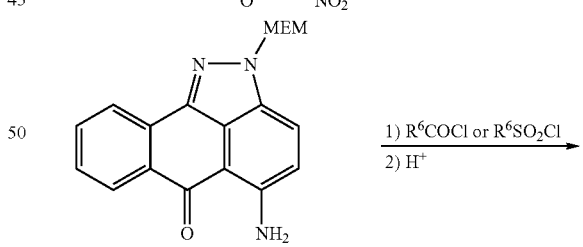

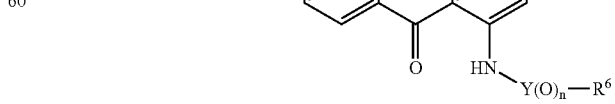

Y = C, n = 1
Y = S, n = 2

A. 5-(Benzoylamino)anthra[1,9cd]pyrazol-6(2H)-one

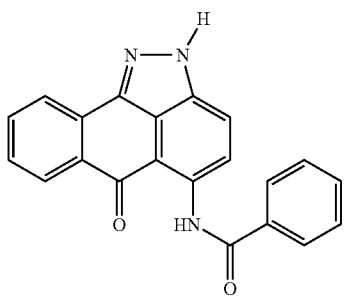

Benzoyl chloride is added to a solution of 2-(methoxyethoxymethyl)-5-aminoanthra[1,9cd]pyrazol-6-(2H)one and triethylamine in methylene chloride at 0° C. The mixture is stirred for 16 hours, quenched with water, and extracted with ethyl acetate (×2). The combined organic layer is washed with sodium bicarbonate solution, and brine, dried and evaporated. The crude reaction mixture is then taken in aqueous 6N hydrochloric acid, and heated at 80° C. for 4 hours. After cooling, the mixture is extracted with ethyl acetate (×2), washed with brine, dried, and evaporated. The residue is chromatographed on silica gel to furnish the desired amide as a yellow solid.

The starting material is prepared as follows. Sodium hexamethyldisilazide is added to a cooled (0° C.) solution of 5-nitroanthra[1,9cd]pyrazol-6(2H)-one (Example 1-D) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-5-nitroanthra[1,9cd]pyrazol-6(2H)-one as an oil.

Palladium (10%) on charcoal and 2-MEM-5-nitroanthra[1,9cd]pyrazol-6(2H)-one in ethanol is placed under 1-atm of hydrogen, and the mixture was stirred for 6 hours. The catalyst is filtered off over celite, and the filtrate is evaporated to dryness to give 2-(methoxyethoxymethyl)-5-aminoanthra[1,9cd]pyrazol-6-(2H)one, which is used without further purification.

B. 5-(Isonicotinylamino)anthra[1,9cd]pyrazol-6(2H)-one

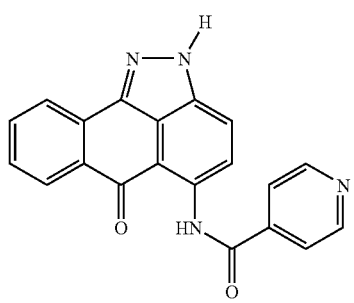

This compound may be made in the same manner using isonicotinoyl chloride as the acid chloride.

C. 5-(Nicotinylamino)anthra[1,9cd]pyrazol-6(2H)-one

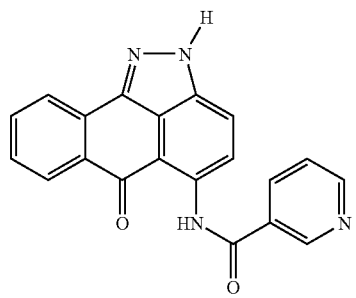

This compound may be made in the same manner using nicotinoyl chloride as the acid chloride.

D. 5-(2-Thiophenecarbonylamino)anthra[1,9cd]pyrazol-6(2H)-one

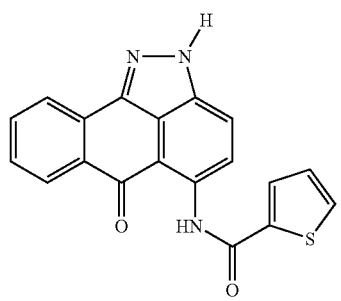

This compound may be made in the same manner using 2-thiophenecarboxylic acid as the acid chloride.

E. 5-(3-Methylbutyrylamino)anthra[1,9cd]pyrazol-6(2H)-one

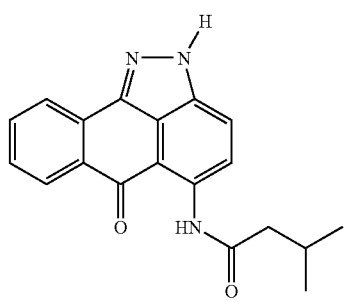

This compound may be made in the same manner using isopentanoyl chloride as the acid chloride.

F. 5-(3-Methanesulfonylamino)anthra[1,9cd]pyrazol-6(2H)-one

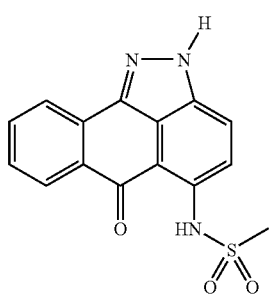

This compound may be made in the same manner using methanesulfonyl chloride as the sulfonyl chloride.

G. 5-(3-Benzenesulfonylamino)anthra[1,9cd]pyrazol-6(2H)-one

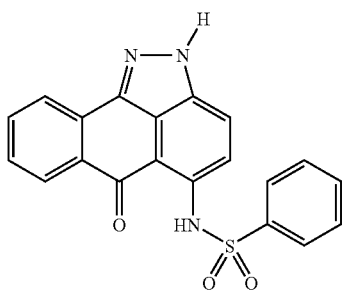

This compound may be made in the same manner using benzenesulfonyl chloride as the sulfonyl chloride.

Example 5

Synthesis of Representative Compounds

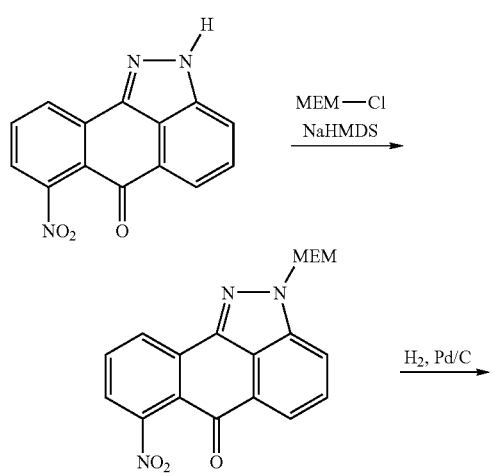

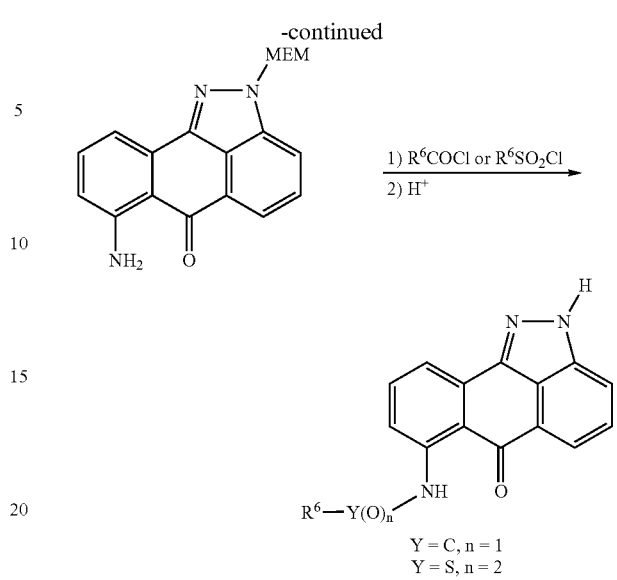

A. 7-(Benzoylamino)anthra[1,9cd]pyrazol-6(2H)-one

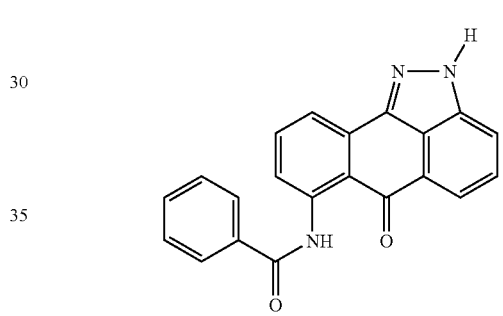

Benzoyl chloride is added to a solution of 2-(methoxyethoxymethyl)-7-aminoanthra[1,9cd]pyrazol-6-(2H)one and triethylamine in methylene chloride at 0° C. The mixture is stirred for 16 hours, quenched with water, and extracted with ethyl acetate (×2). The combined organic layer is washed with sodium bicarbonate solution, and brine, dried and evaporated. The crude reaction mixture is then taken in aqueous 6N hydrochloric acid, and heated at 80° C. for 4 hours. After cooling, the mixture is extracted with ethyl acetate (×2), washed with brine, dried, and evaporated. The residue is chromatographed on silica gel to furnish the desired amide as a yellow solid.

The starting material is prepared as follows. Sodium hexamethyldisilazide is added to a cooled (0° C.) solution of 7-nitroanthra[1,9cd]pyrazol-6(2H)-one (Example 1-E) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1 N hydrochloric acid, and brine, dried and evaporated. The residue is chromatographed on silica gel to give 2-MEM-7-nitroanthra[1,9cd]pyrazol-6(2H)-one as an oil.

Palladium (10%) on charcoal and 2-MEM-5-nitroanthra[1,9cd]pyrazol-6(2H)-one in ethanol is placed under 1-atm of hydrogen, and the mixture was stirred for 6 hours. The catalyst is filtered off over celite, and the filtrate is evaporated to dryness to give 2-(methoxyethoxymethyl)-7-aminoanthra[1,9cd]pyrazol-6-(2H)one, which is used without further purification.

B. 7-(Isonicotinylamino)anthra[1,9cd]pyrazol-6(2H)-one

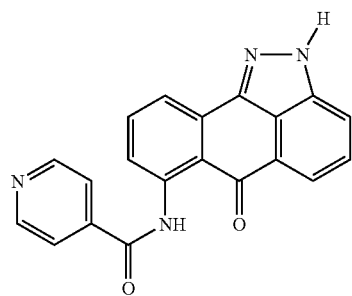

This compound may be made in the same manner using isonicotinoyl chloride as the acid chloride.

C. 7-(Nicotinylamino)anthra[1,9cd]pyrazol-6(2H)-one

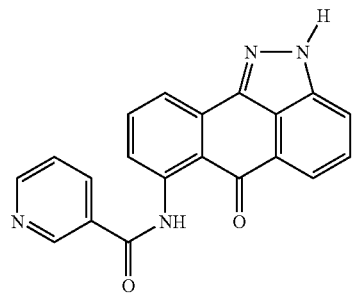

This compound may be made in the same manner using nicotinoyl chloride as the acid chloride.

D. 5-(2-Thiophenecarbonylamino)anthra[1,9cd]pyrazol-6(2H)-one

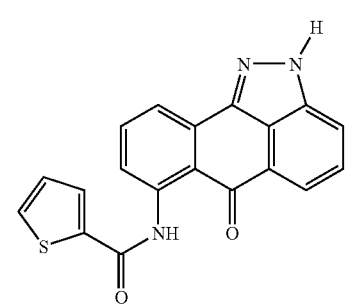

This compound may be made in the same manner using 2-thiophenecarboxylic acid chloride as the acid chloride.

E. 7-(3-Methylbutyrylamino)anthra[1,9cd]pyrazol-6(2H)-one

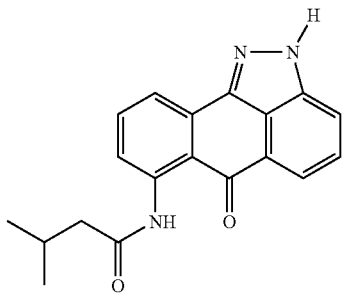

This compound may be made in the same manner using isopentanoyl chloride as the acid chloride.

F. 7-(3-Methanesulfonylamino)anthra[1,9cd]pyrazol-6(2H)-one

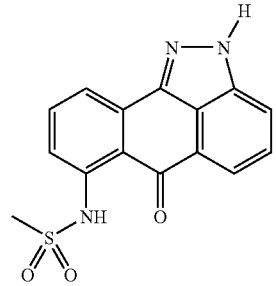

This compound may be made in the same manner using methanesulfonyl chloride as the sulfonyl chloride.

G. 7-(3-Benzenesulfonylamino)anthra[1,9cd]pyrazol-6(2H)-one

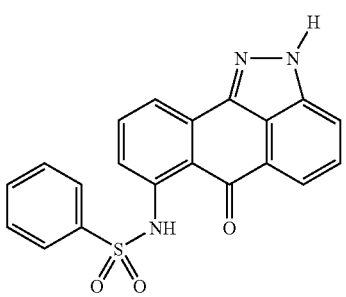

This compound may be made in the same manner using benzenesulfonyl chloride as the sulfonyl chloride.

Example 6

Synthesis of Representative Compounds

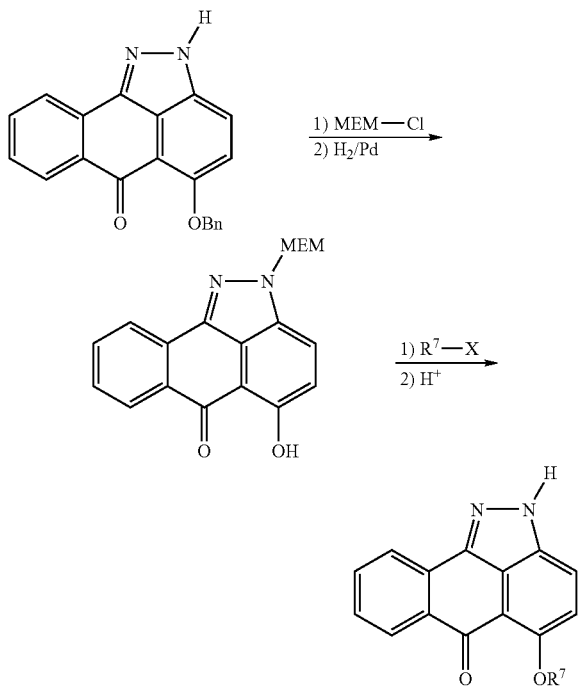

A. 5-(3-Methylbutyloxy)anthra[1,9cd]pyrazol-6(2H)-one

Isopentyl bromide is added to a mixture of 3-(2-methoxyethoxymethyl)5-hydroxyanthra[1,9cd]pyrazol-6(2H)-one and potassium carbonate in dimethylformamide at room temperature. After stirring the mixture for sixteen hours, water is added, and the mixture was extracted with ethyl acetate (×2). The combined organic layer is washed with aqueous sodium bicarbonate, water, 1N hydrochloric acid, and brine, dried and evaporated. The reside is taken in 6N hydrochloric acid and heated at 80° C. for 4 hours. After cooling, the mixture is extracted with ethyl acetate (×2), and the combined organic layer is washed with brine, dried, and evaporated. The residue is purified by column chromatography to afford the title compound as yellow solid.

The starting material is prepared as follows. Sodium hexamethyldisilazide is added to a cooled (0° C.) solution of 5-benzyloxyanthra[1,9cd]pyrazol-6(2H)-one (Example 1-F) in tetrahydrofuran, and the mixture is stirred for 30 minutes at 0° C. MEM-chloride is added, and the mixture is stirred for 16 hours at room temperature. Water is added and the mixture is extracted with ethyl acetate (×2). The combined organic layer is washed with aqueous sodium bicarbonate solution, water, 1 N hydrochloric acid, and brine, dried and evaporated. The residue is chromatographed on silica gel to give 2-MEM-5-benzyloxyanthra[1,9cd]pyrazol-6(2H)-one as an oil.

Palladium(10%) on charcoal and 2-MEM-5-benzyloxyanthra[1,9cd]pyrazol-6(2H)-one in ethanol is placed under 1-atm of hydrogen, and the mixture stirred for 6 hours. The catalyst is filtered off over celite, and the filtrate is evaporated to dryness to give 2-(2-methoxyethoxymethyl)-5-hydroxyanthra[1,9cd]pyrazol-6-(2H)one, which is used without further purification.

B. 5-(4-Pyridylmethoxy)anthra[1,9cd]pyrazol-6(2H)-one

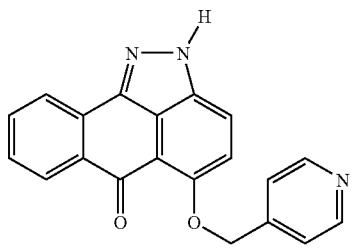

This compound may be made in the same manner using chloromethyl-4-pyridine as the alkyl halide.

C. 5-(3-Pyridylmethoxy)anthra[1,9cd]pyrazol-6(2H)-one

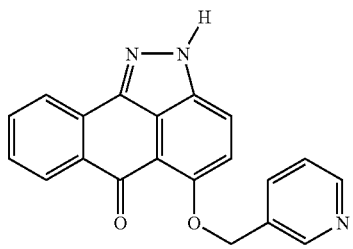

This compound may be made in the same manner using chloromethyl-3-pyridine as the alkyl halide.

D. 5-(2-Methoxyethoxy)anthra[1,9cd]pyrazol-6(2H)-one

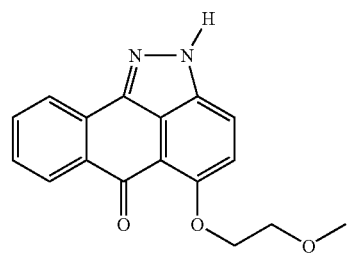

This compound may be made in the same manner using 2-methoxyethyl bromide as the alkyl halide.

E. 5-(2-Dimethylaminoethoxy)anthra[1,9cd]pyrazol-6(2H)-one

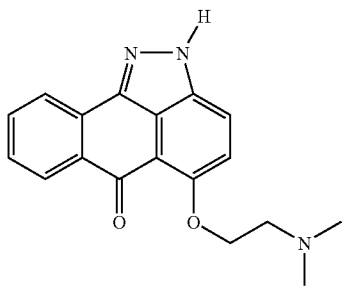

This compound may be made in the same manner using 2-dimethylaminoethyl chloride as the alkyl halide.

Example 7

Synthesis of Representative Compounds

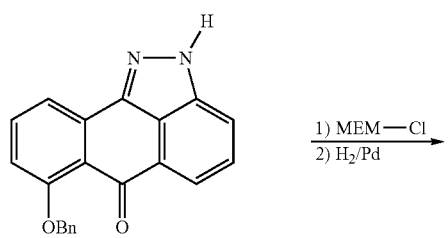

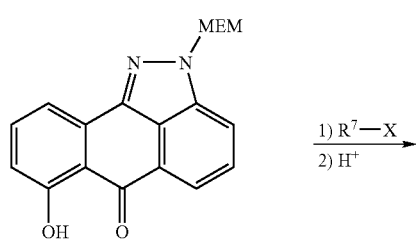

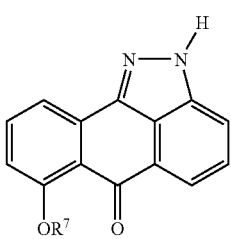

A. 7-(3-Methylbutyloxy)anthra[1,9cd]pyrazol-6(2H)-one

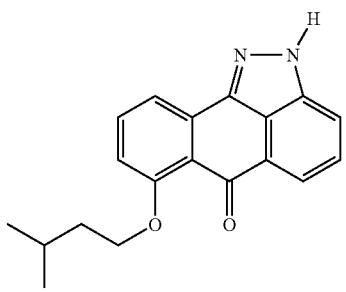

Isopentyl bromide is added to a mixture of 3-(2-methoxyethoxymethyl)-7-hydroxyanthra[1,9cd]pyrazol-6(2H)-one and potassium carbonate in dimethylformamide at room temperature. After stirring the mixture for sixteen hours, water is added, and the mixture was extracted with ethyl acetate (×2). The combined organic layer is washed with aqueous sodium bicarbonate, water, 1 N hydrochloric acid, and brine, dried and evaporated. The residue is taken in 6N hydrochloric acid and heated at 80° C. for 4 hours. After cooling, the mixture is extracted with ethyl acetate (×2), and the combined organic layer is washed with brine, dried, and evaporated. The residue is purified by column chromatography to afford the title compound as yellow solid.

The starting material is prepared as follows. Sodium hexamethyldisilazide is added to a cooled (0° C.) solution of 7-benzyloxyanthra[1,9cd]pyrazol-6(2H)-one (Example 1-F) in tetrahydrofuran, and the mixture is stirred for 30 minutes at 0° C. MEM-chloride is added. and the mixture is stirred for 16 hours at room temperature. Water is added and the mixture is extracted with ethyl acetate (×2). The combined organic layer is washed with aqueous sodium bicarbonate solution, water, 1N hydrochloric acid, and brine, dried and evaporated. The residue is chromatographed on silica gel to give 2-MEM-7-benzyloxyanthra[1,9cd]pyrazol-6(2H)-one as an oil.

Palladium(10%) on charcoal and 2-MEM-7-benzyloxyanthra[1,9cd]pyrazol-6-(2H)-one in ethanol is placed under 1-atm of hydrogen, and the mixture was stirred for 6 h. The catalyst is filtered off over celite, and the filtrate is evaporated to dryness to give 2-(2-methoxyethoxymethyl)-7-hydroxyanthra[1,9cd]pyrazol-6-(2H)one, which is used without further purification.

B. 7-(4-Pyridylmethoxy)anthra[1,9cd]pyrazol-6(2H)-one

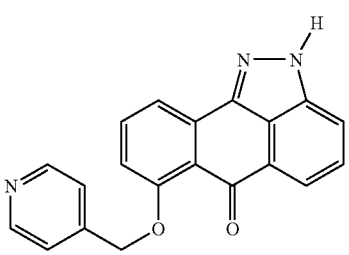

This compound may be made in the same manner using chloromethyl-4-pyridine as the alkyl halide.

C. 7-(3-Pyridylmethoxy)anthra[1,9cd]pyrazol-6(2H)-one

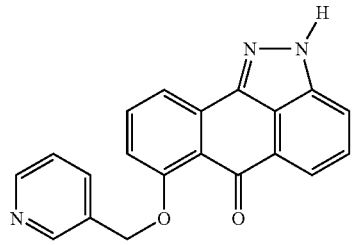

This compound may be made in the same manner using chloromethyl-3-pyridine as the alkyl halide.

D. 7-(2-Methoxyethoxy)anthra[1,9cd]pyrazol-6(2H)-one

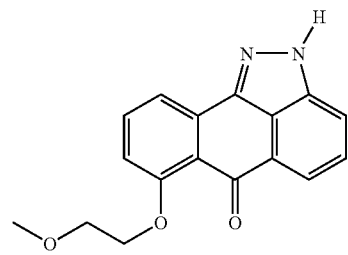

This compound may be made in the same manner using 2-methoxyethyl bromide as the alkyl halide.

E. 7-(2-Dimethylaminoethoxy)anthra[1,9cd]pyrazol-6(2H)-one

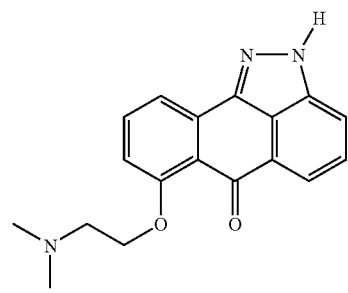

This compound may be made in the same manner using 2-dimethylaminoethyl chloride as the alkyl halide.

Example 8

Activity of Representative Compound

The compounds of this invention may be assayed for their activity accordingly to the following procedures.

JNK Assay

To 10 µL of the test compound in 20% DMSO/80% dilution buffer consisting of 20 mM HEPES (pH 7.6), 0.1 mM EDTA, 2.5 mM magnesium chloride, 0.004% Triton×100, 2 µg/mL leupeptin, 20 mM β-glycerolphosphate, 0.1 mM sodium vanadate, and 2 mM DTT in water is added 30 µL of 50-200 ng His6-JNK1, JNK2 or JNK3 in the same dilution buffer. The mixture is preincubated for 30 minutes at room temperature. Sixty microliter of 10 µg GST-c-Jun (1·79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton×100, 11 µM ATP, and 0.5 µCi γ-32P ATP in water is added and the reaction is allowed to proceed for 1 hour at room temperature. The c-Jun phosphorylation is terminated by addition of 150 µL of 12.5% trichloroacetic acid. After 30 minutes, the precipitate is harvested onto a filter plate, diluted with 50 µL of the scintillation fluid and quantified by a counter. The $IC_{50}$ values are calculated as the concentration of the test compound at which the c-Jun phosphorylation is reduced to 50% of the control value. Preferred compounds of the present invention have an $IC_{50}$ value ranging 0.01-10 µM in this assay. To this end, a preferred compound of this invention is Compound 1, which has an $IC_{50}$ according to this assay of 0.11 µM for JNK1 and JNK2, and 0.15 µM for JNK3.

Selectivity for JNK

Compound 1 was also assayed for its inhibitory activity against the following protein kinases by techniques known to those skilled in this field (see, e.g., *Protein Phosphorlation*, Sefton & Hunter, Eds., Academic Press, pp. 97-367, 1998):

| Enzyme | $IC_{50}$ |
|---|---|
| p38-2 | >30,000 nM |
| ERK 1 | >30,000 nM |
| MEKK 1 | >30,000 nM |
| IKK 1 | >30,000 nM |
| IKK2 | >30,000 nM |
| PKA | >30,000 nM |
| PKC | >10,000 nM |
| EGF-TK | >10,000 nM |

Jurkat T-Cell IL-2 Production Assay

Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of $0.2 \times 10^6$ cells per well in 200 µL of media. Compound stock (20 mM) is diluted in growth media and added to each well as a 10× concentrated solution in a volume of 25 µL, mixed, and allowed to pre-incubate with cells for 30 minutes. The compound vehicle (dimethylsulfoxide) is maintained at a final concentration of 0.5% in all samples; After 30 minutes the cells are activated with PMA (phorbol myristate acetate; final concentration 50 ng/mL) and PHA (phytohemagglutinin; final concentration 2 µg/mL). PMA and PHA are added as a 10× concentrated solution made up in growth media and added in a volume of 25 µL per well. Cell plates are cultured for 10 hours. Cells are pelleted by centrifugation and the media removed and stored at −20° C. Media aliquots are analyzed by sandwich ELISA for the presence of IL-2 as per the manufacturers instructions (Endogen). The $IC_{50}$ values are calculated as the concentration of the test compound at which the IL-2 production was reduced to 50% of the control value. Preferred compounds of the present invention have an $IC_{50}$ value ranging 0.1-30 µM in this assay. FIG. 1 presents the dose dependent inhibition of IL-2 in Jarkat T-Cells by Compound 1 according to this procedure, with a resulting IC$_{50}$ of 5 µM.

Mouse in Vivo LPS-Induced TNF-α A Production Assay

Figure 2:
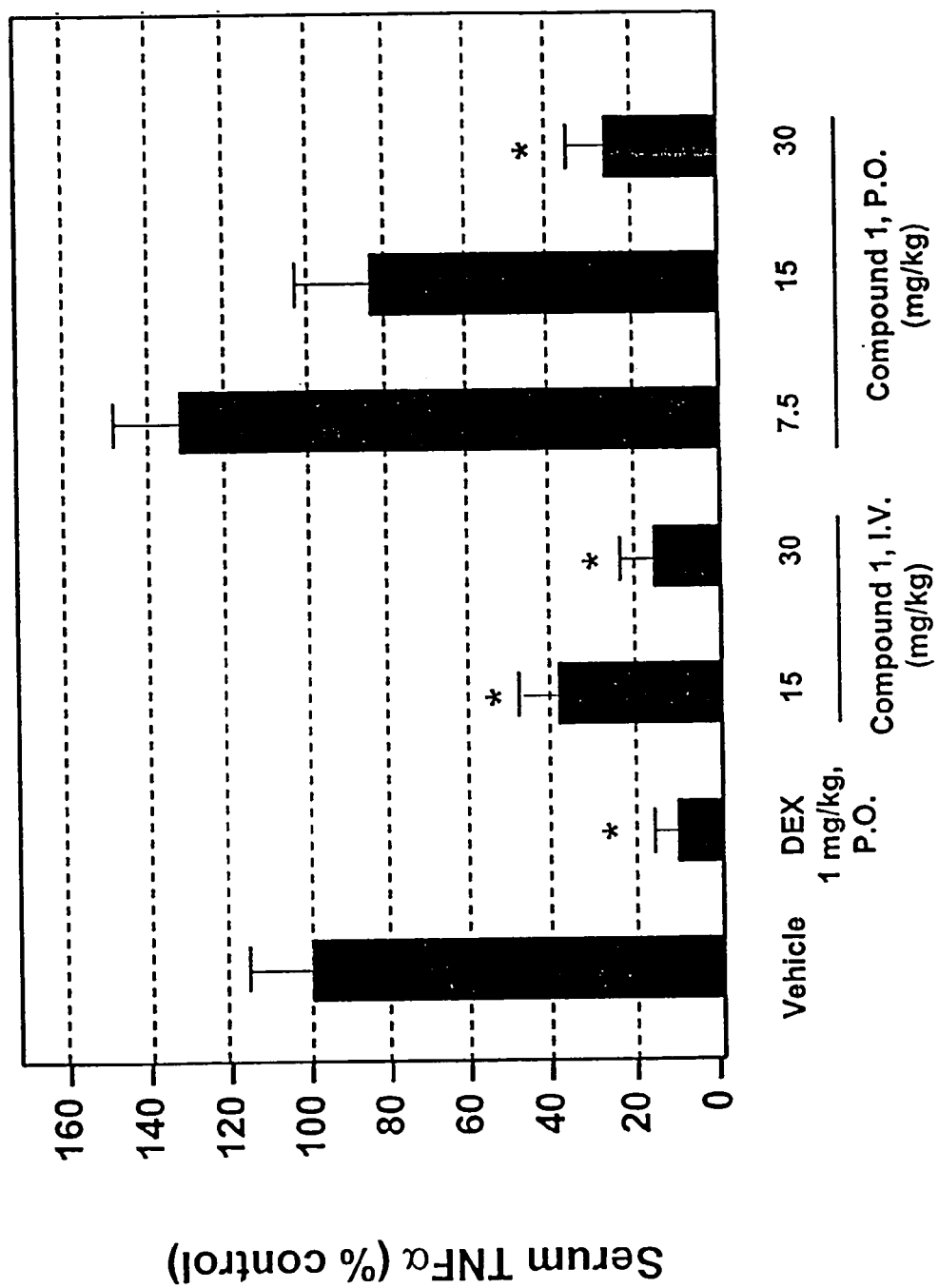
FIG. 2 illustrates the ability of a representative compound of this invention to inhibit TNF-α in a mouse model of endotoxin shock.

Non-fasted mice are acclimatized for at least 7 days. Groups of 4 to 6 female BALB/c or CD-1 mice (8-10 weeks of age from Charles River laboratories) are pretreated with test compound, either by intravenous injection or by oral gavage 15-180 minutes prior to the injection of 0.5 mg/kg Bacto LPS from E. coli 055:B5 (Difco Labs). Ninety minutes after LPS challenge, a terminal bleed is performed via abdominal vena cava and blood is allowed to clot at room temperature for 30 minutes in Microtainer serum separator tubes. After separation by centrifugation, the serum is stored frozen at −80° C. ELISA is performed on thawed, diluted samples (1:10 to 1:20) using a Mouse TNF-alpha kit (Biosource International). The ED$_{50}$ values are calculated as the dose of the test compound at which the TNF-α production is reduced to 50% of the control value. Preferred compounds of the present invention have an ED$_{50}$ value ranging 1-30 mg/kg in this assay. FIG. 2 illustrates the results of this experiment utilizing Compound 1 administered by intravenous injection (I.V.) at 15 and 30 mg/kg, as well as by per os (P.O.) at 7.5, 15 and 30 mg/kg. Vehicle alone (PEG-400, propylene glycol, cremophor EL, and ethanol in normal saline, "PPCES") and dexamethasone-21 acetate ("DEX") (1 mg/kg P.O.) were run as controls (n=6, *=p0.01). Compound 1 was administered 15 minutes pre-LPS challenge, and bleed occurred 90 minutes post LPS.

Inhibition of Leukocyte Recruitment in Rat Inflamed Lung

Figure 3:
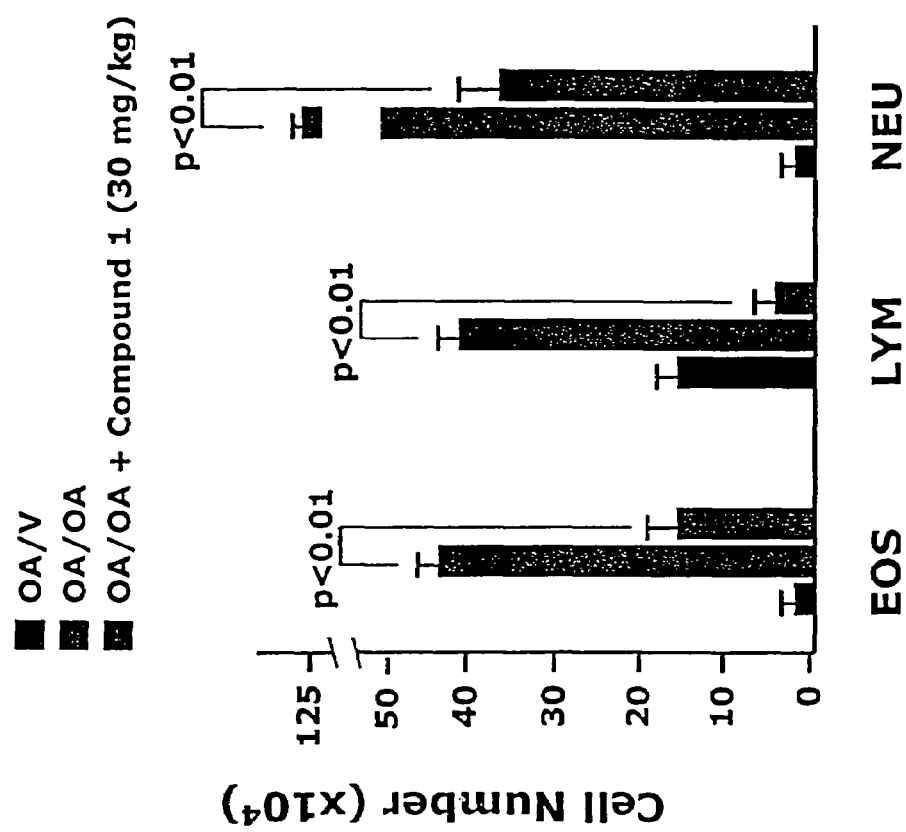
FIG. 3 illustrates the ability of a representative compound of this invention to inhibit leukocyte recruitment in rat model for inflamed lung.

Aerosol administration of ovalbumin in Brown Norway Rats previously sensitized by injection of ovalbumin (OA) results in an allergic airway inflammation marked by the generation of an eosinophil- and T-lymphocyte-rich leukocytic infiltration in the lungs (see Richards et al., Am. J. Physiol. 271:2 Pt 1, L267-76, 1996). Compound 1 was administered by subcutaneous injection at a dose of 30 mg/kg, b.i.d. for 3 days prior to ovalbumin challenge by aerosol. Cell counts were obtained from samples of bronchoalveolar lavage, the results of which are illustrated in FIG. 3 (V=PPCES vehicle).

Rat in Vivo Adjuvant Arthritis

Figure 4A:
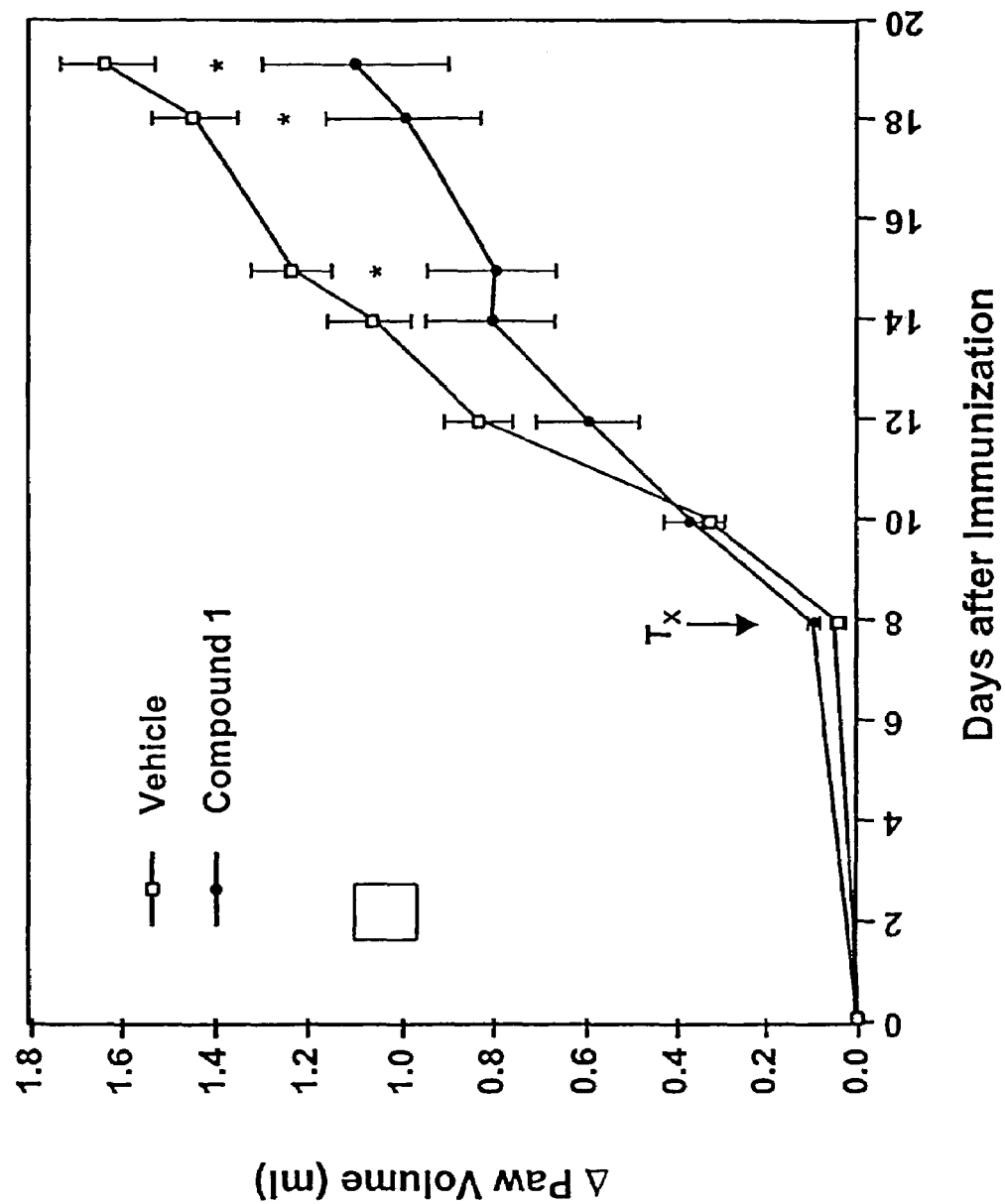
FIGS. 4A-D illustrate the ability of a representative compound of this invention to inhibit paw swelling (FIG. 4A), joint destruction (FIG. 4B), transcription factor AP-1 activation (FIG. 4C), and expression of MMP-13 (FIG. 4D) in a rat model for adjuvant arthritis.
Figure 4B:
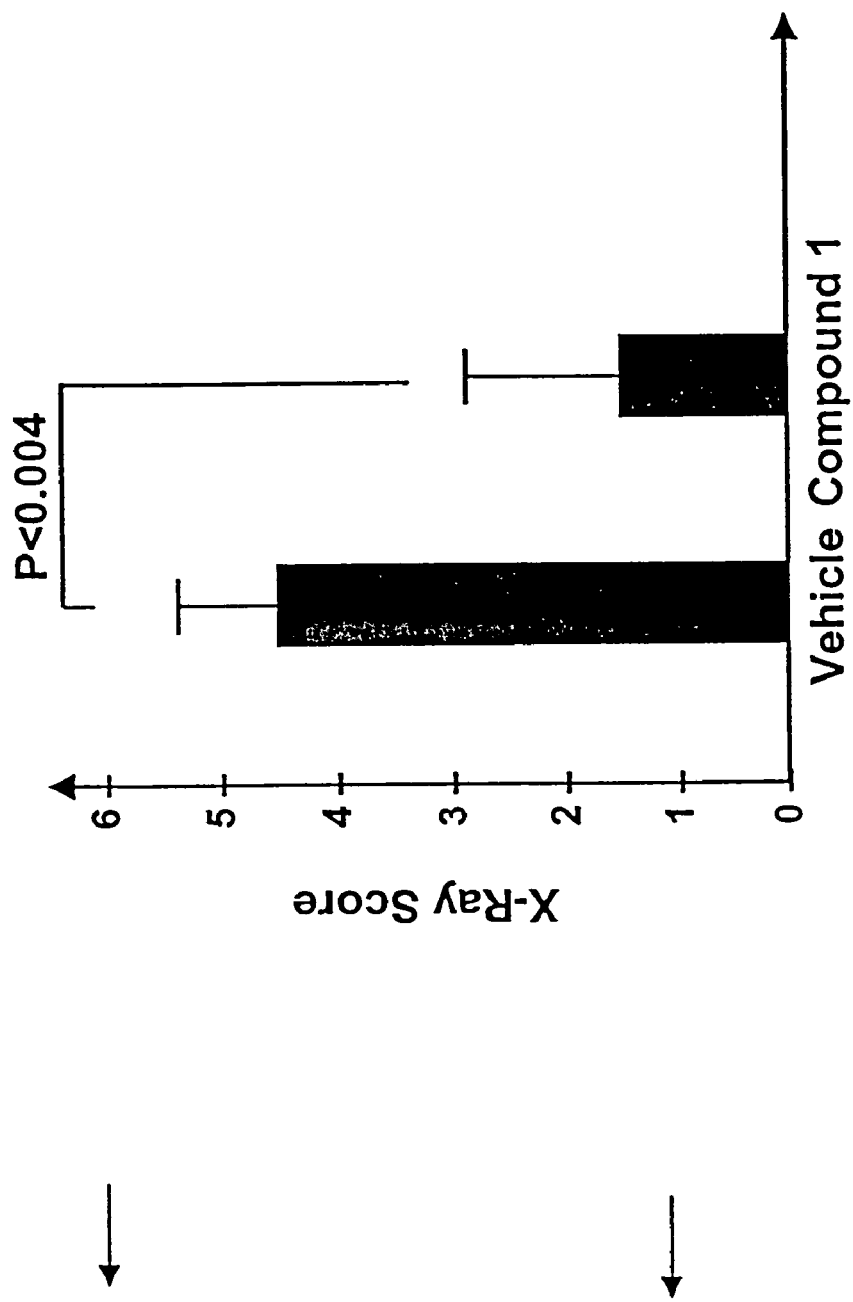
Figure 4C:
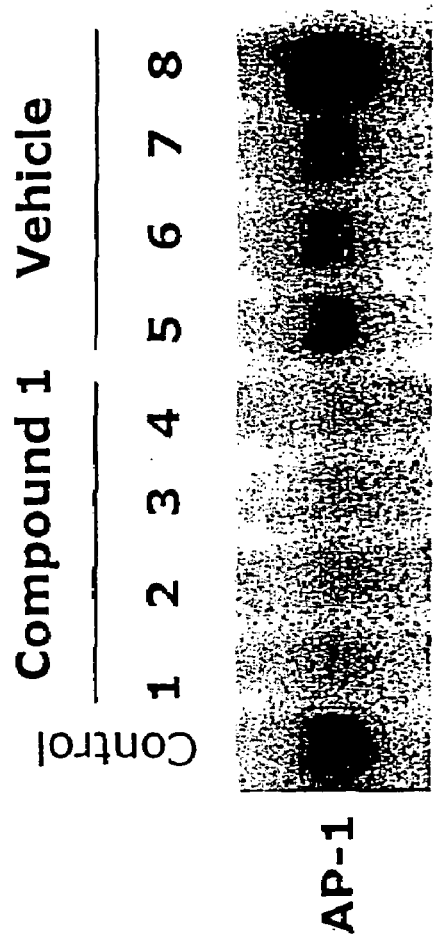
Figure 4D:
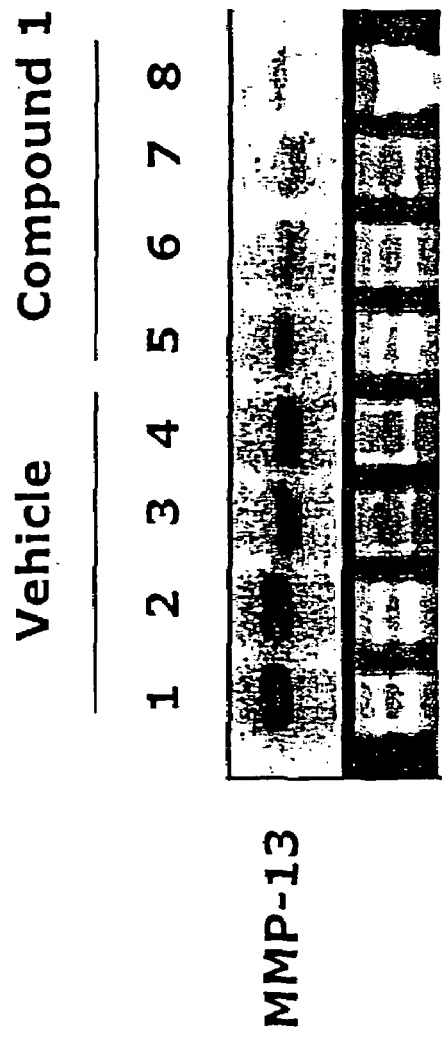

Male Lewis rats were immunized with complete Freund's adjuvant on day 0 to induce an aggressive arthritis characterized by joint destruction and paw swelling. Compound 1 was administered subcutaneously once daily from day 8 to day 20. Paw swelling was determined be water displacement plethysmometry (see FIG. 4A; *=p<0.01). Radiographs were obtained of the right hind paw to assess bone changes using semi-quantitative scoring system: demineralization (0-2+), calcaneal erosion (0-1+), and heterotropic bone formation (0-1+), with a maximum possible score=6 (see FIG. 4B). Activation of AP-1 (see FIG. 4C) was determined by DNA binding activity in an electrophoretic mobility shift assay (EMSA) (Ausubel et al., Short Protocols in Molecular Biology, Second Edition, John Wiley & Sons Publisher, New York, 1992). Matrix metalloproteinase-13 expression (see FIG. 4D) was measured by northern blot analysis of MMP-13 mRNA (Ausebel et al., supra) (see also Winter et al., Arthritis and Rheumatism 9(3):394-404, 1966; Weichman et al., Pharmacological Methods in the Control of Inflammation, Chang and Lewis Eds., Alan R. Liss, Inc., Publ., New York, 1989).

Kainic Acid-Induced Seizure Response

Figure 5:
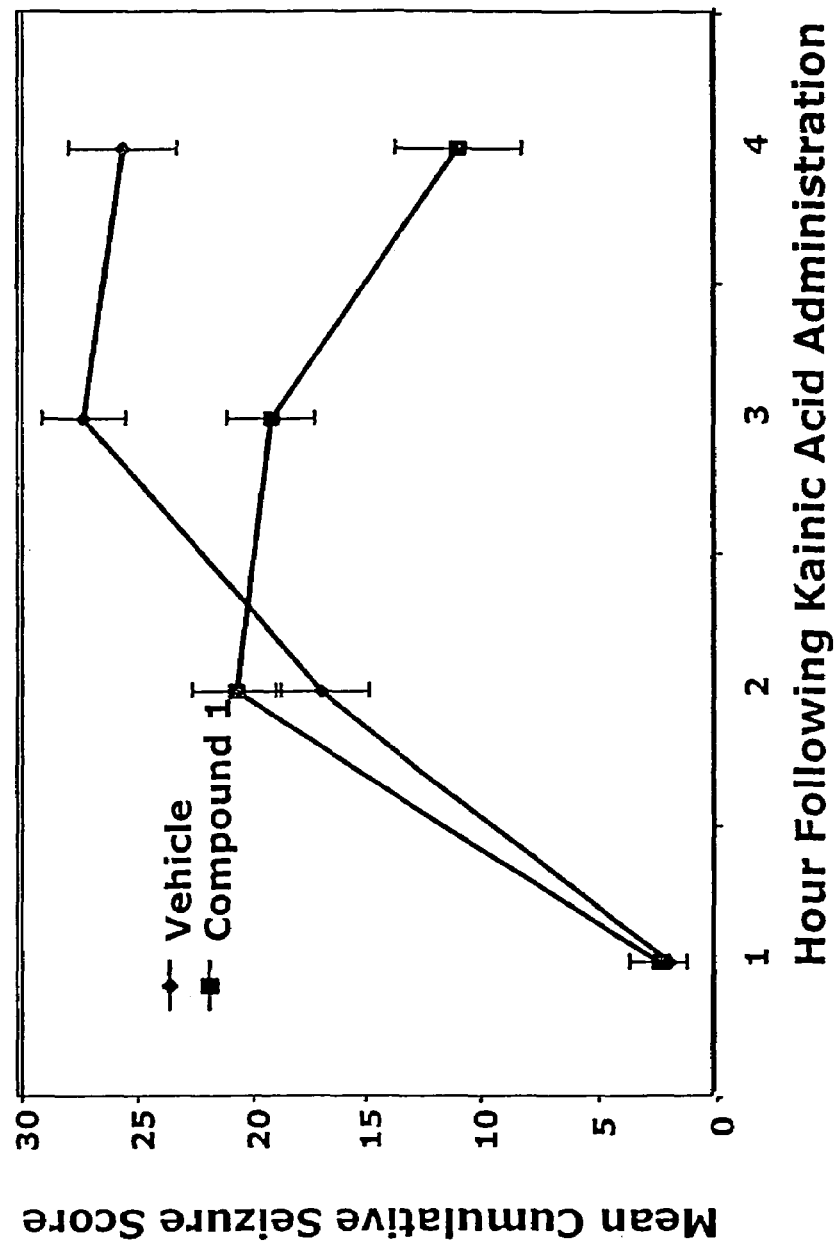
FIG. 5 illustrates the ability of a representative compound of this invention to reduce kainic acid-induced seizure response.

Compound 1 was administered to male CD rats at 10 mg/kg intravenously through a tail vein catheter. This was followed immediately by a 30 mg/kg subcutaneous injection. Vehicle controls received the same injection volumes of the PPCES vehicle alone. Thirty minutes later, animals were given a 1-mg/kg i.p. injection of kainic acid in normal saline solution. This dose of kainic acid has been previously reported to induce a seizure syndrome in rats (Maj et al., Eur. J. Pharm. 359:27-32, 1992). Seizure behavior was monitored for 4 hours following kainic acid injection. As presented in FIG. 5, behaviors were assessed based on the following cumulative scoring system: 1 pt.=arrest of motion; 2 pts.=myoclonic jerks of the head and neck (moderate); 3 pts.=unilateral or bilateral forelimb clonic activity; 4 pts.=whole body clonus; 5 pts.=clonic-tonic seizures; 6 pts.=status epilepticus (see also Mathis and Ungerer, Exp. Brain Res. 88:277-282, 1992; Rong et al., Proc. Natl. Acad. Sci. USA 96:9897-9902, 1999; Yang et al., Nature 389:865-870, 1997).

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A method for treating an inflammatory condition, comprising administering to a patient in need thereof an effective amount of a compound having the structure:

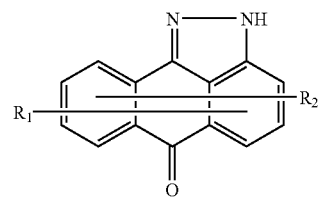

or a pharmaceutically acceptable salt thereof,
wherein
R$_1$ and R$_2$ are absent or present and independently represent a group represented by formula (a):

(a)

R$_3$ and R$_4$ taken together represent alkylidene or a heteroatom-containing alkylidene, or R$_3$ and R$_4$ are the same or different and independently represent hydrogen, alkyl, cycloalkyl, aryl, arylalkyl, cycloalkylalkyl, aryloxyalkyl, alkoxyalkyl, alkoxyamino, or alkoxy (mono- or di-alkylamino);
wherein the inflammatory condition is Type II diabetes or obesity.

2. The method of claim 1 wherein the treating or preventing comprises inhibiting JNK in vivo.

3. The method of claim 2 wherein inhibiting JNK in vivo comprises inhibiting TNF-α in vivo.

4. The method of claim 1 wherein the compound has the following structure:

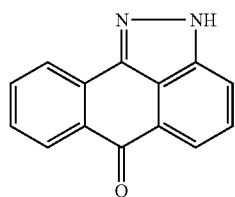

or a pharmaceutically acceptable salt thereof.

5. The method of claim 1 wherein the compound has one of the following structures:

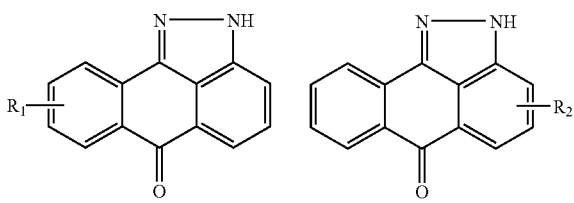

or a pharmaceutically acceptable salt thereof.

6. The method of claim 1 wherein the compound has one of the following structres:

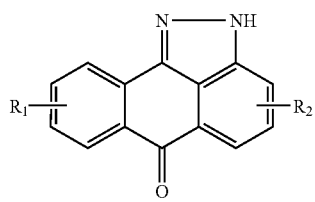

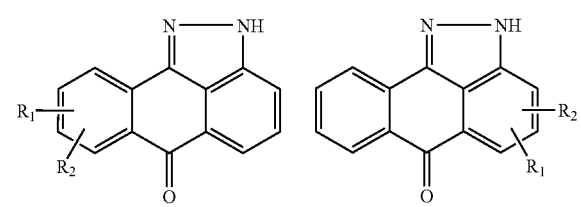

or a pharmaceutically acceptable salt thereof.

* * * * *